(12) United States Patent
Choi-Sledeski et al.

(10) Patent No.: US 8,183,231 B2
(45) Date of Patent: May 22, 2012

(54) SUBSTITUTED PROPANE PHOSPHINIC ACID DERIVATIVES

(75) Inventors: Yong Mi Choi-Sledeski, Belle Mead, NJ (US); Julian Levell, Bernardsville, NJ (US); Gregory Bernard Poli, Bethlehem, PA (US); Mark Czekaj, Doylestown, PA (US); Alan John Collis, Lexington, MA (US); Roy Vaz, Branchburg, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 1519 days.

(21) Appl. No.: 11/552,346

(22) Filed: Oct. 24, 2006

(65) Prior Publication Data

US 2007/0060502 A1 Mar. 15, 2007

Related U.S. Application Data

(63) Continuation of application No. PCT/US2005/019657, filed on Jun. 3, 2005.

(60) Provisional application No. 60/577,394, filed on Jun. 4, 2004.

(51) Int. Cl.
  *A61K 31/675* (2006.01)
  *A61K 31/66* (2006.01)
  *C07F 9/30* (2006.01)

(52) U.S. Cl. .............. 514/91; 514/94; 514/119; 562/15; 548/119; 548/412

(58) Field of Classification Search ............ 514/94, 514/91, 119; 562/15; 548/119, 412
See application file for complete search history.

(56) References Cited

U.S. PATENT DOCUMENTS 5,190,933 A 3/1993 Baylis et al.

FOREIGN PATENT DOCUMENTS

WO WO 99/37606 7/1999
WO WO 99/51613 10/1999

OTHER PUBLICATIONS

Vippagunta et al. Advanced Drug Delivery Reviews, vol. 48, pp. 3-26 (2001).*
Waldmeier et al., Br. J. Pharmacol. 1994), 113, 1515-1521.*
Ezra, A., et. al., A Peptide Prodrug Approach for Improving Bisphosphonate Oral Absorption, Journal Med. Chem. (2000, pp. 3641-3652, vol. 43).
Friedrichsen, G.M., et. al., Model Prodrugs Designed for the Intestinal Peptide Transporter. A Synthetic Approach for Coupling of Hydroxy-Containing Compounds to Dipeptides, European journal of Pharmaceutical Sciences vol. 14, (2001) 13-19.

* cited by examiner

*Primary Examiner* — Peter O Sullivan
(74) *Attorney, Agent, or Firm* — Kelly L. Bender

(57) ABSTRACT

The present invention relates to a series of substituted 3-aminopropane phosphinic acid derivatives of formula I:

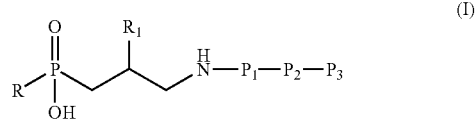

wherein R, $R_1$, $P_1$, $P_2$ and $P_3$ are as defined herein. The compounds of this invention are useful in treating a variety of diseases including but not limited to depression, anxiety, certain psychiatric symptoms, cognitive impairment and schizophrenia.

34 Claims, No Drawings

SUBSTITUTED PROPANE PHOSPHINIC ACID DERIVATIVES

CROSS REFERENCE TO RELATED APPLICATIONS

This application is a continuation of International application No. PCT/US2005/019,657, filed Jun. 3, 2005, which claims the benefit of U.S. Provisional Application No. 60/577,394, filed Jun. 4, 2004; both of which are incorporated herein by reference in their entirety.

BACKGROUND OF THE INVENTION

1. Field of the Invention

The present invention relates to a series of substituted 3-aminopropane phosphinic acid derivatives. More specifically, the present invention relates to a series of 3-amino-peptidyl-2-hydroxypropane-cyclohexylmethyl phosphinic acid derivatives. This invention also relates to methods of making these compounds. The compounds of this invention are transformed in vivo into biologically active compounds and are, therefore, useful as pharmaceutical agents, especially in the treatment and/or prevention of a variety of diseases including diseases associated with the central nervous system.

2. Description of the Art

U.S. Pat. No. 5,190,933 discloses certain substituted propane phosphinic compounds having therapeutic utility in treating various disorders including cognition and memory disorders, anxiety and depression. However, a problem posed by these compounds is their poor bioabsorption. It has also been reported in the literature that certain compounds such as bisphosphonates exhibit poor absorption from the GI tract. In fact, only one percent of the oral dose is absorbed. As a result, a series of peptidyl prodrugs of these bisphosphonates have been made and shown to improve the drug absorption. See, Ezra, et al., J. Med. Chem. 2000, 43, 3641.

It has also been reported that human peptide transporter, hPepT1, situated in the small intestine, may be exploited among others to increase absorption of drugs or model drugs by attaching them to a dipeptide. A synthetic protocol has also been suggested to attach a dipeptide to model drugs containing a hydroxy group. See Friedrichsen et al., Eur. J. Pharm. 2001, 14, 13.

International Publication No. WO99/51613 discloses prodrugs of phosphorus containing pharmaceuticals. The compounds disclosed therein are derived from a phosphonate, phosphinate or phosphoryl function having at least two functional moieties. These compounds have been claimed to exhibit enhanced bioavailability or other pharmacokinetic performance relative to the parent drug.

All of the references described herein are incorporated herein by reference in their entirety.

However, there have been no reports in the literature that prodrugs of above mentioned propane phosphinic compounds can also be similarly made. Further, it has not been reported that peptidyl prodrugs, especially, mono-, di- and tri-peptidyl derivatives of 3-amino-2-hydroxypropane phosphinic compounds may offer improved bioabsorption properties.

Accordingly, it is an object of this invention to provide a series of 3-amino-peptidyl-2-hydroxypropane-cyclohexylmethyl phosphinic acid derivatives that exhibit improved bioavailability relative to the parent compound.

It is also an object of this invention to provide processes for the preparation of 3-amino-peptidyl-2-hydroxypropane-cyclohexylmethyl phosphinic acid derivatives as disclosed herein.

Other objects and further scope of the applicability of the present invention will become apparent from the detailed description that follows.

SUMMARY OF THE INVENTION

Thus in accordance with this invention there is provided a compound, including enantiomers, stereoisomers, and tautomers of said compound and pharmaceutically acceptable salts, solvates or derivatives thereof, with said compound having the general structure shown in formula I:

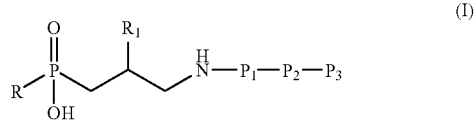

wherein:
R is $C_{1-8}$alkyl, $C_{3-8}$cycloalkyl$C_{1-4}$alkyl, aryl$C_{1-4}$alkyl or fluoroalkyl of the formula $C_nH_xF_y$, wherein n is an integer from 1 to 4, x is an integer from 0 to 8, y is an integer from 1 to 9 and sum of x and y is 2n+1;
$R_1$ is hydrogen or hydroxy;
$P_1$ and $P_2$ are the same or different and independently of each other selected from the group consisting of a bond, Gly, D- or L-Ala, Ile, Leu, Lys, Phe, Pro, Trp, Tyr, Val, Nva, Nle, Sar, Ser, bAla, bVal, Met, Orn, Thr, Cys, His, Arg, Asp, Glu, Asn and Gln; and
$P_3$ is Gly, D- or L-Ala, Ile, Leu, Lys, Phe, Pro, Trp, Tyr, Val, Nva, Nle, Sar, Ser, bAla, bVal, Met, Orn, Thr, Cys, His, Arg, Asp, Glu, Asn and Gln.

The compounds of this invention can be formulated into pharmaceutical compositions and are useful in treating a variety of disease states including but not limited to depression, bipolar disorders, anxiety disorders, psychiatric symptoms, cognitive impairment or memory disorders, and schizophrenia.

DETAILED DESCRIPTION OF THE INVENTION

The terms as used herein have the following meanings:

As used herein, the expression "$C_{1-8}$alkyl" includes methyl and ethyl groups, and straight-chained or branched propyl, butyl, pentyl, hexyl, heptyl and octyl groups. Particular alkyl groups are methyl, ethyl, n-propyl, isopropyl, n-butyl, isobutyl and tert-butyl, etc.

As used herein, the expression "$C_{3-8}$cycloalkyl" means substituted or unsubstituted three to eight membered cyclic aliphatic compounds. Specific examples include cyclopropyl, cyclobutyl, cyclohexyl, cycloheptyl and cyclooctyl.

As used herein, the expression "$C_{3-8}$cycloalkyl$C_{1-4}$alkyl" means that the cycloalkyl is further attached to $C_{1-4}$alkyl as defined herein. Representative examples include cyclopropylmethyl, cyclobutylmethyl, cyclopentylmethyl, cyclohexylmethyl, cyclohexylethyl and the like.

As used herein, the expression "fluoroalkyl of the formula $C_nH_xF_y$, wherein n is an integer from 1 to 4, x is an integer from 0 to 8, y is an integer from 1 to 9 and sum of x and y is 2n+1" means that one or more of the hydrogen atoms in said alkyl group is replaced with fluorine atoms. Specific examples include mono-, di- and trifluoromethyl, mono-, di-, tri-, tetraand pentafluoroethyl, and straight-chained or branched mono-, di-, tri-, tetra-, penta-, hexa- and heptafluoropropyl, and mono-, di-, tri-, tetra-, penta-, hexa-, hepta-, octa- and nonafluorobutyl groups.

As used herein, the expression "aryl" means substituted or unsubstituted phenyl or naphthyl. Specific examples of substituted phenyl or naphthyl include o-, p-, m-tolyl, 1,2-, 1,3-, 1,4-xylyl, 1-methylnaphthyl, 2-methylnaphthyl, etc. "Substituted phenyl" or "substituted naphthyl" also include any of the possible substituents as further defined herein or one known in the art.

As used herein, the expression "aryl$C_{1-4}$alkyl" means that the aryl is further attached to $C_{1-4}$alkyl as defined herein. Representative examples include benzyl, phenylethyl, 2-phenylpropyl, 1-naphthylmethyl, 2-naphthylmethyl and the like.

As used herein, "patient" means a warm blooded animal, such as for example rat, mice, dogs, cats, guinea pigs, and primates such as humans.

As used herein, the expression "pharmaceutically acceptable carrier" means a non-toxic solvent, dispersant, excipient, adjuvant, or other material which is mixed with the compound of the present invention in order to permit the formation of a pharmaceutical composition, i.e., a dosage form capable of administration to the patient. One example of such a carrier is pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist substantially anhydrous or can be hydrated. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts, and salts formed with suitable organic ligands, e.g. quaternary ammonium salts.

As used herein, the term "prodrug" shall have the generally accepted meaning in the art. One such definition includes a pharmacologically inactive chemical entity that when metabolized or chemically transformed by a biological system such as a mammalian system is converted into a pharmacologically active substance.

The expression "stereoisomers" is a general term used for all isomers of the individual molecules that differ only in the orientation of their atoms in space. Typically it includes mirror image isomers that are usually formed due to at least one asymmetric center, (enantiomers). Where the compounds according to the invention possess two or more asymmetric centers, they may additionally exist as diastereoisomers, also certain individual molecules may exist as geometric isomers (cis/trans). Similarly, certain compounds of this invention may exist in a mixture of two or more structurally distinct forms that are in rapid equilibrium, commonly known as tautomers. Representative examples of tautomers include keto-enol tautomers, phenol-keto tautomers, nitroso-oxime tautomers, imine-enamine tautomers, etc. It is to be understood that all such isomers and mixtures thereof in any proportion are encompassed within the scope of the present invention.

The term "solvate" as used herein means that an aggregate that consists of a solute ion or molecule with one or more solvent molecules. Similarly, a "hydrate" means that a solute ion or molecule with one or more water molecules.

In a broad sense, the term "substituted" is contemplated to include all permissible substituents of organic compounds. In a few of the specific embodiments as disclosed herein, the term "substituted" means substituted with one or more substituents independently selected from the group consisting of $C_{1-6}$alkyl, $C_{2-6}$alkenyl, $C_{1-6}$perfluoroalkyl, phenyl, hydroxy, —$CO_2H$, an ester, an amide, $C_1$-$C_6$alkoxy, $C_1$-$C_6$thioalkyl, $C_1$-$C_6$perfluoroalkoxy, —$NH_2$, Cl, Br, I, F, —NH-lower alkyl, and —N(lower alkyl)$_2$. However, any of the other suitable substituents known to one skilled in the art can also be used in these embodiments.

"Therapeutically effective amount" means an amount of the compound which is effective in treating the named disease, disorder or condition.

The term "treating" refers to:
 (i) preventing a disease, disorder or condition from occurring in a patient that may be predisposed to the disease, disorder and/or condition, but has not yet been diagnosed as having it;
 (ii) inhibiting the disease, disorder or condition, i.e., arresting its development; and
 (iii) relieving the disease, disorder or condition, i.e., causing regression of the disease, disorder and/or condition.

Unless otherwise stated, the α-amino acids used in the preparation of the compounds of this invention are preferably in their L-configuration; however, it is contemplated that the amino acids used in the compounds of formula I can be of either the D- or L-configurations or can be mixture of the D- and L-isomers, including racemic mixture, which becomes more clear from the detailed description of the invention that follows below. The recognized abbreviations for the α-amino acids are set forth in Table 1.

TABLE 1

| AMINO ACID | SYMBOL |
|---|---|
| Alanine | Ala |
| Arginine | Arg |
| Asparagine | Asn |
| Aspartic Acid | Asp |
| beta-Alanine | bAla |
| beta-Valine | bVal |
| Cysteine | Cys |
| Glutamic Acid | Glu |
| Glutamine | Gln |
| Glycine | Gly |
| Histidine | His |
| Isoleucine | Ile |
| Leucine | Leu |
| Lysine | Lys |
| Methionine | Met |
| Norleucine | Nle |
| Norvaline | Nva |
| Ornithine | Orn |
| Phenylalanine | Phe |

TABLE 1-continued

| AMINO ACID | SYMBOL |
| --- | --- |
| Proline | Pro |
| Sarcosine | Sar |
| Serine | Ser |
| Threonine | Thr |
| Tryptophan | Trp |
| Tyrosine | Tyr |
| Valine | Val |

Thus, in accordance with the practice of this invention there is provided a compound, including enantiomers, stereoisomers, and tautomers of said compound and pharmaceutically acceptable salts, solvates or derivatives thereof, with said compound having the general structure shown in formula I:

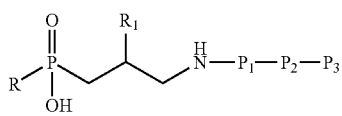
(I)

wherein:
R is $C_{1-8}$alkyl, $C_{3-8}$cycloalkyl$C_{1-4}$alkyl, aryl$C_{1-4}$alkyl or fluoroalkyl of the formula $C_nH_xF_y$, wherein n is an integer from 1 to 4, x is an integer from 0 to 8, y is an integer from 1 to 9 and sum of x and y is 2n+1;
$R_1$ is hydrogen or hydroxy;
$P_1$ and $P_2$ are the same or different and independently of each other selected from the group consisting of a bond, Gly, D- or L-Ala, Ile, Leu, Lys, Phe, Pro, Trp, Tyr, Val, Nva, Nle, Sar, Ser, bAla, bVal, Met, Orn, Thr, Cys, His, Arg, Asp, Glu, Asn and Gln; and
$P_3$ is Gly, D- or L-Ala, Ile, Leu, Lys, Phe, Pro, Trp, Tyr, Val, Nva, Nle, Sar, Ser, bAla, bVal, Met, Orn, Thr, Cys, His, Arg, Asp, Glu, Asn and Gln.

Particularly preferred R groups are methyl, butyl, cyclohexylmethyl, benzyl, fluoromethyl, difluoromethyl and trifluoromethyl.

In an embodiment of this invention the compound of formula I wherein R is cyclohexylmethyl is particularly preferred. Further, in this embodiment $R_1$ is hydroxy. Thus in accordance with this embodiment, the compound of this aspect of the invention is represented by formula IA:

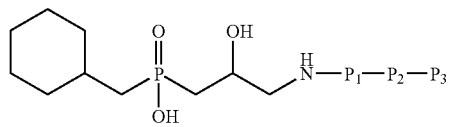
(IA)

In another embodiment of this invention, the compound of this invention is a stereospecific isomer of formula IB:

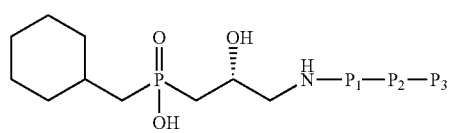
(IB)

wherein $P_1$, $P_2$ and $P_3$ are as defined above.

In yet another embodiment of this invention the compounds of this invention are mono-peptides of formula IC:

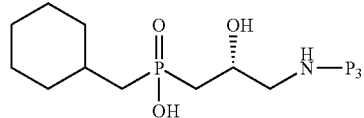
(IC)

Thus, in this aspect of the invention both $P_1$ and $P_2$ are bonds. Further, in this aspect of the invention $P_3$ is Gly, L-Ala, L-Leu, L-Ile, L-Phe, L-Pro, L-Val, L-Thr, L-Glu, L-His, L-Tyr, L-Asp and L-Asn.

More preferably $P_3$ is Gly, L-Ala, L-Leu, L-Ile, L-Phe, L-Thr, and L-Val. Even more preferably $P_3$ is Gly, L-Ala, L-Ile, L-Thr, and L-Val. Most preferably, in this embodiment of the invention, $P_3$ is Gly, L-Thr, and L-Val.

As representative examples of mono-peptidic compounds of formula I of this invention, without any limitation, the following compounds may be enumerated:
[(R)-3-((S)-2-amino-3-methyl-butyrylamino)-2-hydroxy-propyl]-cyclohexylmethyl-phosphinic acid;
[(R)-3-(2-amino-acetylamino)-2-hydroxy-propyl]-cyclohexylmethyl-phosphinic acid;
[(R)-3-((S)-2-amino-propionylamino)-2-hydroxy-propyl]-cyclohexylmethyl-phosphinic acid;
[(R)-3-((R)-2-amino-3-methyl-butyrylamino)-2-hydroxy-propyl]-cyclohexylmethyl-phosphinic acid;
[(R)-3-((S)-2-amino-4-methyl-pentanoylamino)-2-hydroxy-propyl]-cyclohexylmethyl-phosphinic acid;
[(R)-3-((S)-2-amino-3-methyl-pentanoylamino)-2-hydroxy-propyl]-cyclohexylmethyl-phosphinic acid;
cyclohexylmethyl-{(R)-2-hydroxy-3-[((S)-pyrrolidine-2-carbonyl)-amino]-propyl}-phosphinic acid;
[(R)-3-((S)-2-amino-3-hydroxy-butyrylamino)-2-hydroxy-propyl]-cyclohexylmethyl-phosphinic acid;
[(R)-3-((S)-2-amino-3-phenyl-propionylamino)-2-hydroxy-propyl]-cyclohexylmethyl-phosphinic acid trifluoroacetate;
[(R)-3-((R)-2-amino-propionylamino)-2-hydroxy-propyl]-cyclohexylmethyl-phosphinic acid;
(S)-4-amino-4-[(R)-3-(cyclohexylmethyl-hydroxy-phosphinoyl)-2-hydroxy-propylcarbamoyl]-butyric acid;
{(R)-3-[(S)-2-amino-3-(1H-imidazol-4-yl)-propionylamino]-2-hydroxy-propyl}-cyclohexylmethyl-phosphinic acid;
{(R)-3-[(S)-2-amino-3-(4-hydroxy-phenyl)-propionylamino]-2-hydroxy-propyl}-cyclohexylmethyl-phosphinic acid;
[(R)-3-((S)-2-amino-3-carbamoyl-propionylamino)-2-hydroxy-propyl]-cyclohexylmethyl-phosphinic acid; and
a pharmaceutically acceptable salt, hydrate or solvate thereof.

In another preferred embodiment of this invention, the following specific mono-peptidic compounds within the scope of formula I may be mentioned:
[(R)-3-((S)-2-amino-3-methyl-butyrylamino)-2-hydroxy-propyl]-cyclohexylmethyl-phosphinic acid;
[(R)-3-(2-amino-acetylamino)-2-hydroxy-propyl]-cyclohexylmethyl-phosphinic acid;
[(R)-3-((S)-2-amino-propionylamino)-2-hydroxy-propyl]-cyclohexylmethyl-phosphinic acid;
[(R)-3-((S)-2-amino-4-methyl-pentanoylamino)-2-hydroxy-propyl]-cyclohexylmethyl-phosphinic acid;

[(R)-3-((S)-2-amino-3-methyl-pentanoylamino)-2-hydroxy-propyl]-cyclohexylmethyl-phosphinic acid;

[(R)-3-((S)-2-amino-3-hydroxy-butyrylamino)-2-hydroxy-propyl]-cyclohexylmethyl-phosphinic acid;

[(R)-3-((S)-2-amino-3-phenyl-propionylamino)-2-hydroxy-propyl]-cyclohexylmethyl-phosphinic acid trifluoroacetate; and a pharmaceutically acceptable salt, hydrate or solvate thereof.

In a preferred embodiment, the following mono-peptidic compounds falling within the scope of compound of formula I are disclosed:

[(R)-3-((S)-2-amino-3-methyl-butyrylamino)-2-hydroxy-propyl]-cyclohexylmethyl-phosphinic acid;

[(R)-3-(2-amino-acetylamino)-2-hydroxy-propyl]-cyclohexylmethyl-phosphinic acid;

[(R)-3-((S)-2-amino-propionylamino)-2-hydroxy-propyl]-cyclohexylmethyl-phosphinic acid;

[(R)-3-((S)-2-amino-3-methyl-pentanoylamino)-2-hydroxy-propyl]-cyclohexylmethyl-phosphinic acid;

[(R)-3-((S)-2-amino-3-hydroxy-butyrylamino)-2-hydroxy-propyl]-cyclohexylmethyl-phosphinic acid; and a pharmaceutically acceptable salt, hydrate or solvate thereof.

Particularly preferred mono-peptidic compounds of this invention are further set forth below:

[(R)-3-((S)-2-amino-3-methyl-butyrylamino)-2-hydroxy-propyl]-cyclohexylmethyl-phosphinic acid or a pharmaceutically acceptable salt, hydrate or solvate thereof;

[(R)-3-(2-amino-acetylamino)-2-hydroxy-propyl]-cyclohexylmethyl-phosphinic acid or a pharmaceutically acceptable salt, hydrate or solvate thereof; and

[(R)-3-((S)-2-amino-3-hydroxy-butyrylamino)-2-hydroxy-propyl]-cyclohexylmethyl-phosphinic acid or a pharmaceutically acceptable salt, hydrate or solvate thereof.

In another embodiment of this invention the compounds of this invention are di-peptidic compounds of formula ID:

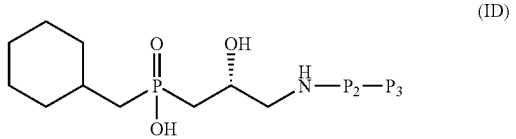

(ID)

Thus in accordance with this aspect of the invention $P_1$ is a bond in compounds of formula I. Further, in this aspect of the invention:

$P_2$ is Gly, L-Ala, L-Val, L-Phe, L-Leu, L-Pro, L-Ile, L-Thr, L-Trp, L-Tyr and L-His; and $P_3$ is Gly, L-Ala, D-Ala, L-Leu, D-Leu, L-Ele, D-Ile, L-Phe, L-Pro, L-Val, D-Val, L-Thr, L-Glu, L-His, D-Glu, L-Trp, L-Tyr and L-Asn.

In a preferred embodiment of this aspect of the invention:

$P_2$ is Gly, L-Ala, L-Val, L-Phe, L-Leu, L-Pro, L-Ile, L-Thr and L-His; and $P_3$ is Gly, L-Ala, L-Leu, L-Ile, L-Phe, L-Pro, L-Val, L-Thr, L-Glu, L-His, L-Trp, L-Tyr and L-Asn.

In a more preferred embodiment of this aspect of the invention:

$P_2$ is Gly, L-Ala, L-Val, L-Pro and L-Phe; and $P_3$ is Gly, L-Ala, L-Val, L-Phe, L-Thr, L-His, L-Trp and L-Tyr.

Most preferably, in an embodiment of this aspect of the invention:

$P_2$ is Gly, L-Ala, L-Val, L-Pro and L-Phe; and $P_3$ is L-Ala and L-Val.

Listed below are the illustrative examples of di-peptidic compounds within the scope of formula I of this invention:

{(R)-3-[(S)-2-((S)-2-amino-propionylamino)-3-methyl-butyrylamino]-2-hydroxy-propyl}-cyclohexylmethyl-phosphinic acid;

{(R)-3-[(R)-2-((S)-2-amino-propionylamino)-3-methyl-butyrylamino]-2-hydroxy-propyl}-cyclohexylmethyl-phosphinic acid;

{(R)-3-[(S)-2-(2-amino-acetylamino)-3-methyl-butyrylamino]-2-hydroxy-propyl}-cyclohexylmethyl-phosphinic acid;

{(R)-3-[(S)-2-((S)-2-amino-3-methyl-butyrylamino)-4-methyl-pentanoylamino]-2-hydroxy-propyl}-cyclohexylmethyl-phosphinic acid;

{(R)-3-[(R)-2-((S)-2-amino-3-methyl-butyrylamino)-4-methyl-pentanoylamino]-2-hydroxy-propyl}-cyclohexylmethyl-phosphinic acid;

{(R)-3-[(S)-2-((S)-2-amino-3-methyl-butyrylamino)-3-methyl-pentanoylamino]-2-hydroxy-propyl}-cyclohexylmethyl-phosphinic acid;

{(R)-3-[(R)-2-((S)-2-amino-3-methyl-butyrylamino)-3-methyl-pentanoylamino]-2-hydroxy-propyl}-cyclohexylmethyl-phosphinic acid;

{(R)-3-[2-((S)-2-amino-3-methyl-butyrylamino)-acetylamino]-2-hydroxy-propyl}-cyclohexylmethyl-phosphinic acid hydrate;

{(R)-3-[(S)-2-((S)-2-amino-3-methyl-butyrylamino)-propionylamino]-2-hydroxy-propyl}-cyclohexylmethyl-phosphinic acid hydrate;

{(R)-3-[(R)-2-((S)-2-amino-3-methyl-butyrylamino)-propionylamino]-2-hydroxy-propyl}-cyclohexylmethyl-phosphinic acid hydrate;

{(R)-3-[(S)-2-((S)-2-amino-3-phenyl-propionylamino)-methyl-butyrylamino]-2-hydroxy-propyl}-cyclohexylmethyl-phosphinic acid;

{(R)-3-[(R)-2-((S)-2-Amino-3-phenyl-propionylamino)-3-methyl-butyrylamino]-2-hydroxy-propyl}-cyclohexylmethyl-phosphinic acid;

{(R)-3-[(S)-2-((S)-2-amino-3-methyl-butyrylamino)-3-methyl-butyrylamino]-2-hydroxy-propyl}-cyclohexylmethyl-phosphinic acid;

{(R)-3-[(R)-2-((S)-2-amino-3-methyl-butyrylamino)-3-methyl-butyrylamino]-2-hydroxy-propyl}-cyclohexylmethyl-phosphinic acid;

{(R)-3-[(S)-2-((S)-2-amino-4-methyl-pentanoylamino)-3-methyl-butyrylamino]-2-hydroxy-propyl}-cyclohexylmethyl-phosphinic acid;

cyclohexylmethyl-((R)-2-hydroxy-3-{(S)-3-methyl-2-[((S)-pyrrolidine-2-carbonyl)-amino]-butyrylamino}-propyl)-phosphinic acid;

{(R)-3-[(S)-2-((S)-2-amino-3-methyl-pentanoylamino)-3-methyl-butyrylamino]-2-hydroxy-propyl}-cyclohexylmethyl-phosphinic acid;

(S)-2-{(R)-2-amino-4-[(R)-3-(cyclohexylmethyl-hydroxy-phosphinoyl)-2-hydroxy-propylcarbamoyl]-butyrylamino}-propionic acid;

{(R)-3-[(S)-2-((S)-2-amino-3-methyl-butyrylamino)-3-phenyl-propionylamino]-2-hydroxy-propyl}-cyclohexylmethyl-phosphinic acid;

{(R)-3-[(S)-2-((S)-2-amino-3-methyl-butyrylamino)-3-(4-hydroxy-phenyl)-propionylamino]-2-hydroxy-propyl}-cyclohexylmethyl-phosphinic acid;

((R)-3-{[(S)-1-((S)-2-amino-3-methyl-butyryl)-pyrrolidine-2-carbonyl]-amino}-2-hydroxy-propyl)-cyclohexylmethyl-phosphinic acid;

((R)-3-{(S)-2-[(S)-2-amino-3-(1H-indol-3-yl)-propionylamino]-3-methyl-butyrylamino}-2-hydroxy-propyl)-cyclohexylmethyl-phosphinic acid;

((R)-3-{(S)-2-[(S)-2-amino-3-(4-hydroxy-phenyl)-propionylamino]-3-methyl-butyrylamino}-2-hydroxy-propyl)-cyclohexylmethyl-phosphinic acid;

{(R)-3-[(S)-2-((S)-2-amino-3-methyl-butyrylamino)-3-(1H-indol-3-yl)-propionylamino]-2-hydroxy-propyl}-cyclohexylmethyl-phosphinic acid;

cyclohexylmethyl-((R)-2-hydroxy-3-{(S)-3-phenyl-2-[((S)-pyrrolidine-2-carbonyl)-amino]-propionylamino}-propyl)-phosphinic acid hydrochloride;

((R)-3-{(S)-2-[(S)-2-amino-3-(1H-imidazol-4-yl)-propionylamino]-3-methyl-butyrylamino}-2-hydroxy-propyl)-cyclohexylmethyl-phosphinic acid;

{(R)-3-[(R)-2-((R)-2-amino-3-methyl-butyrylamino)-3-methyl-butyrylamino]-2-hydroxy-propyl}-cyclohexylmethyl-phosphinic acid; and {(R)-3-[(S)-2-((R)-2-amino-3-methyl-butyrylamino)-3-methyl-butyrylamino]-2-hydroxy-propyl}-cyclohexylmethyl-phosphinic acid;

{(R)-3-[(R)-2-((R)-2-amino-3-methyl-butyrylamino)-propionylamino]-2-hydroxy-propyl}-cyclohexylmethyl-phosphinic acid;

{(R)-3-[(S)-2-((R)-2-amino-3-methyl-butyrylamino)-propionylamino]-2-hydroxy-propyl}-cyclohexylmethyl-phosphinic acid; and a pharmaceutically acceptable salt, hydrate or solvate thereof.

In another embodiment of this invention the following di-peptidic compounds are preferred:

{(R)-3-[(S)-2-((S)-2-amino-propionylamino)-3-methyl-butyrylamino]-2-hydroxy-propyl}-cyclohexylmethyl-phosphinic acid;

{(R)-3-[(S)-2-(2-amino-acetylamino)-3-methyl-butyrylamino]-2-hydroxy-propyl}-cyclohexylmethyl-phosphinic acid;

{(R)-3-[(S)-2-((S)-2-amino-3-methyl-butyrylamino)-4-methyl-pentanoylamino]-2-hydroxy-propyl}-cyclohexylmethyl-phosphinic acid;

{(R)-3-[(S)-2-((S)-2-amino-3-methyl-butyrylamino)-3-methyl-pentanoylamino]-2-hydroxy-propyl}-cyclohexylmethyl-phosphinic acid;

{(R)-3-[2-((S)-2-amino-3-methyl-butyrylamino)-acetylamino]-2-hydroxy-propyl}-cyclohexylmethyl-phosphinic acid hydrate;

{(R)-3-[(S)-2-((S)-2-amino-3-methyl-butyrylamino)-propionylamino]-2-hydroxy-propyl}-cyclohexylmethyl-phosphinic acid hydrate;

{(R)-3-[(S)-2-((S)-2-amino-3-phenyl-propionylamino)-3-methyl-butyrylamino]-2-hydroxy-propyl}-cyclohexylmethyl-phosphinic acid;

{(R)-3-[(S)-2-((S)-2-amino-3-methyl-butyrylamino)-3-methyl-butyrylamino]-2-hydroxy-propyl}-cyclohexylmethyl-phosphinic acid;

{(R)-3-[(S)-2-((S)-2-amino-4-methyl-pentanoylamino)-3-methyl-butyrylamino]-2-hydroxy-propyl}-cyclohexylmethyl-phosphinic acid;

cyclohexylmethyl-((R)-2-hydroxy-3-{(S)-3-methyl-2-[((S)-pyrrolidine-2-carbonyl)-amino]-butyrylamino}-propyl)-phosphinic acid;

{(R)-3-[(S)-2-((S)-2-amino-3-methyl-pentanoylamino)-methyl-butyrylamino]-2-hydroxy-propyl}-cyclohexylmethyl-phosphinic acid;

{(R)-3-[(S)-2-((S)-2-amino-3-methyl-butyrylamino)-3-phenyl-propionylamino]-2-hydroxy-propyl}-cyclohexylmethyl-phosphinic acid;

{(R)-3-[(S)-2-((S)-2-amino-3-methyl-butyrylamino)-3-(4-hydroxy-phenyl)-propionylamino]-2-hydroxy-propyl}-cyclohexylmethyl-phosphinic acid;

((R)-3-{[(S)-1-((S)-2-amino-3-methyl-butyryl)-pyrrolidine-2-carbonyl]-amino}-2-hydroxy-propyl)-cyclohexylmethyl-phosphinic acid;

((R)-3-{(S)-2-[(S)-2-amino-3-(1H-indol-3-yl)-propionylamino]-3-methyl-butyrylamino}-2-hydroxy-propyl)-cyclohexylmethyl-phosphinic acid;

((R)-3-{(S)-2-[(S)-2-amino-3-(4-hydroxy-phenyl)-propionylamino]-3-methyl-butyrylamino}-2-hydroxy-propyl)-cyclohexylmethyl-phosphinic acid;

{(R)-3-[(S)-2-((S)-2-amino-3-methyl-butyrylamino)-3-(1H-indol-3-yl)-propionylamino]-2-hydroxy-propyl}-cyclohexylmethyl-phosphinic acid;

cyclohexylmethyl-((R)-2-hydroxy-3-{(S)-3-phenyl-2-[((S)-pyrrolidine-2-carbonyl)-amino]-propionylamino}-propyl)-phosphinic acid hydrochloride;

((R)-3-{(S)-2-[(S)-2-amino-3-(1H-imidazol-4-yl)-propionylamino]-3-methyl-butyrylamino}-2-hydroxy-propyl)-cyclohexylmethyl-phosphinic acid;

{(R)-3-[(S)-2-((R)-2-Amino-3-methyl-butyrylamino)-3-methyl-butyrylamino]-2-hydroxy-propyl}-cyclohexylmethyl-phosphinic acid;

{(R)-3-[(S)-2-((R)-2-amino-3-methyl-butyrylamino)-propionylamino]-2-hydroxy-propyl}-cyclohexylmethyl-phosphinic acid; and a pharmaceutically acceptable salt, hydrate or solvate thereof.

Particularly preferred di-peptidic compounds of this invention are set forth below:

{(R)-3-[(S)-2-((S)-2-amino-propionylamino)-3-methyl-butyrylamino]-2-hydroxy-propyl}-cyclohexylmethyl-phosphinic acid or a pharmaceutically acceptable salt, hydrate or solvate thereof;

{(R)-3-[2-((S)-2-amino-3-methyl-butyrylamino)-acetylamino]-2-hydroxy-propyl}-cyclohexylmethyl-phosphinic acid hydrate or a pharmaceutically acceptable salt, hydrate or solvate thereof;

{(R)-3-[(S)-2-((S)-2-amino-3-methyl-butyrylamino)-propionylamino]-2-hydroxy-propyl}-cyclohexylmethyl-phosphinic acid hydrate or a pharmaceutically acceptable salt, hydrate or solvate thereof; and {(R)-3-[(S)-2-((S)-2-amino-3-methyl-butyrylamino)-3-methyl-butyrylamino]-2-hydroxy-propyl}-cyclohexylmethyl-phosphinic acid or a pharmaceutically acceptable salt, hydrate or solvate thereof.

In yet another embodiment, the compounds of this invention are tri-peptides of formula IA or IB as described herein. Thus, in this aspect of the invention, the compound of formula I is having:

$P_1$ is Gly, L-Ala, D-Ala, L-Ile, D-Ile, L-Leu, D-Leu, L-Lys, L-Phe, L-Pro, L-Trp, L-Tyr, L-Val, D-Val, L-Nle, L-Met, L-Orn, L-Thr, L-Cys, L-His, L-Arg, L-Glu, D-Glu, L-Asn and L-Gln; and $P_2$ and $P_3$ are the same or different and independently of each other selected from the group consisting of: Gly, L-Ala, L-Ile, L-Leu, L-Lys, L-Phe, L-Pro, L-Trp, L-Tyr, L-Val, L-Nle, L-Ser, L-Met, L-Orn, L-Thr, L-Cys, L-His, L-Arg, L-Asp, L-Glu, L-Asn and L-Gln.

In a preferred embodiment of this aspect of the invention:

$P_1$ is Gly, L-Ala, L-Leu, L-Ile, L-Phe, L-Pro, L-Val, L-Thr, L-Glu, L-His, L-Trp, L-Tyr and L-Asn; and $P_2$ and $P_3$ are the same or different and independently of each other selected from the group consisting of: Gly, L-Ala, L-Val, L-Phe, L-Leu, L-Pro, L-Ile, L-Trp, L-Tyr and L-His.

In a more preferred embodiment of this aspect of the invention:

$P_1$ is Gly, L-Ala, L-Leu, L-Ile, L-Phe, L-Pro, L-Val, L-Thr, L-Glu, L-His, L-Trp, L-Tyr and L-Asn; and $P_2$ and $P_3$ are the same or different and independently of each other selected from the group consisting of: L-Ala, L-Val, L-Phe, L-Leu, L-Pro, and L-His.

In a most preferred embodiment of this aspect of the invention:

$P_1$ is Gly, L-Ala, L-Val, L-Thr, L-Glu, L-His, L-Trp, L-Tyr and L-Asn; and $P_2$ and $P_3$ are the same or different and independently of each other selected from the group consisting of: Gly, L-Ala, L-Val and L-Phe.

Representative examples of tri-peptidic compounds of formula I of this invention, without any limitation are enumerated below:

((R)-3-{(S)-2-[(S)-2-((S)-2-amino-3-methyl-butyrylamino)-3-methyl-butyryl-amino]-3-methyl-butyrylamino}-2-hydroxy-propyl)-cyclohexylmethyl-phosphinic acid;

((R)-3-{(S)-2-[2-(2-amino-acetylamino)-acetylamino]-3-methyl-butyrylamino}-2-hydroxy-propyl)-cyclohexyl-metthyl-phosphinic acid; and a pharmaceutically acceptable salt, hydrate or solvate thereof.

The compounds of this invention can be synthesized by any of the procedures known to one skilled in the art. Specifically, several of the starting materials used in the preparation of the compounds of this invention are known or are themselves commercially available. The compounds of this invention and several of the precursor compounds may also be prepared by methods used to prepare similar compounds as reported in the literature and as further described herein.

More specifically, the parent compound 1, ((R)-3-amino-2-hydroxy-propyl)-cyclohexylmethyl-phosphinic acid, can be synthesized by any of the procedures reported in the literature. For example, its synthesis is reported in U.S. Pat. No. 5,300,679 as well as in the articles of Froestl et al., J. Med. Chem. 1995, 38, 3297-3312, and Froestl et al., J. Med. Chem. 1995, 38, 3313-3331; all of which are incorporated herein by reference in their entirety. The compounds of formula IA or formula IB as disclosed herein can be synthesized according to the following procedures of Schemes 1 and 2, wherein the $P_1$, $P_2$ and $P_3$ are as defined hereinabove unless otherwise indicated. It should be understood that various other compounds within the scope of formula I can also be synthesized in a similar fashion following the procedures of either Scheme 1 or 2 and employing suitable starting materials.

Scheme 1

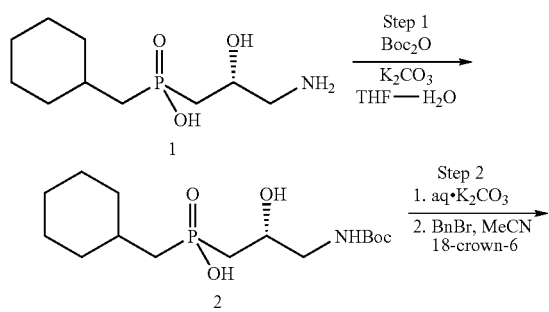

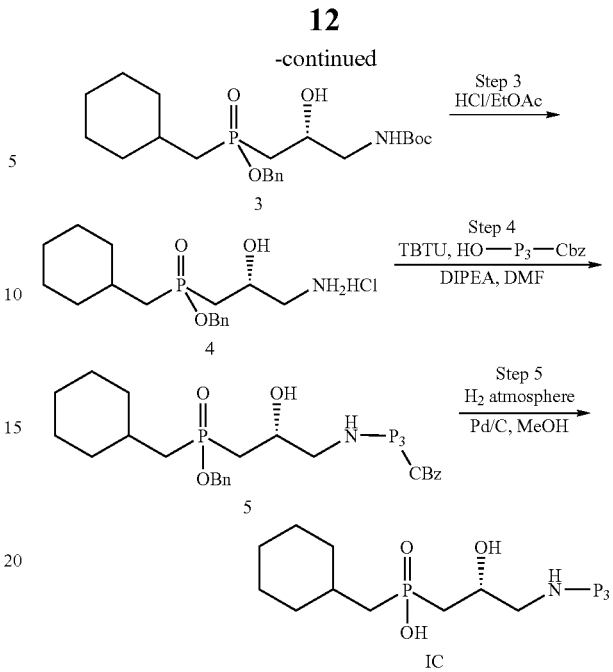

Scheme 1 illustrates synthetic procedures that can be employed for the preparation of mono-peptidic compounds of this invention, wherein both $P_1$ and $P_2$ are bonds. Various modifications can be made using other procedures known in the art which is readily appreciated by one skilled in the art. In Step 1, Scheme 1, the amino group of compound 1 is protected by tert-butyloxycarbonyl (Boc) by reacting with di-tert-butyl-dicarbonate ($Boc_2O$) in the presence of a suitable base such as potassium carbonate to afford amino-protected compound 2. This reaction is generally carried out at ambient reaction temperatures in a suitable organic solvent or a mixture of solvents, such as THF and water. Various other amino functional groups can similarly be employed in this reaction. See for example T. W. Greene, Protective Groups in Organic Synthesis, J. Wiley-Interscience Publication (1991).

In Step 2, Scheme 1, the phosphinic acid group is similarly protected by reacting compound 2 with a suitable acid protecting group such as benzyl bromide (BnBr) to afford compound 3. This reaction is generally carried out in the presence of a base such as potassium carbonate and a suitable catalyst such as 18-crown-6 in an organic solvent such as acetonitrile (MeCN). The reaction is generally carried out at reflux temperature of the solvent but lower temperatures can also be employed depending upon the nature of the starting material.

In Step 3, Scheme 1, compound 3 is subjected to suitable reaction conditions in order to deprotect the amino function. Generally, such deprotection reactions are carried out at sub-ambient temperatures, e.g., at about 0° C. in the presence of an acid such as hydrochloric acid in a suitable organic solvent such as ethyl acetate to afford compound 4 as amine hydrochloride.

In Step 4, Scheme 1, compound 4 is reacted with suitable amino-protected amino acid. Various amino protecting groups can be employed to protect the amino functional group of the amino acid, such as benzyloxycarbonyl (Cbz). This reaction can be carried out under variety of reaction conditions. For instance, this reaction is carried out in the presence of a suitable base such as diisopropylethylamine (DIPEA) and a suitable coupling agent such as 2-(1H-benzotriazol-1-yl)-1,1,3,3-tetramethyluronium tetrafluoroborate (TBTU) in a suitable organic solvent such as dimethylformamide (DMF). Generally, the reaction is carried out at ambient reaction temperature conditions but sub-ambient as well as super-ambient temperature conditions can also be employed depending upon the nature of the starting materials employed in order to obtain compound 5.

Finally, in Step 5, Scheme 1, the amino and phosphinic acid protected compound 5 is subjected to deprotection reaction in order to obtain compound of formula IC in which $P_1$ and $P_2$ are bonds. The deprotection is generally carried out under hydrogenation conditions by subjecting compound 5 to hydrogen atmosphere in the presence of a suitable catalyst such as palladium on carbon. Various other known deprotection conditions can also be employed.

Scheme 2 illustrates synthetic procedures that can be used for the preparation of di-peptidic and tri-peptidic compounds of this invention. Again, various modifications that are known in the art can be used in the preparation of these compounds and Scheme 2 is provided here for illustrative purposes only and not to be construed in any way that limits the scope of the present invention.

tidic compounds of this invention can be prepared as illustrated in Steps 1B and 2B of Scheme 2.

Alternatively, the di-peptidic as well as the tri-peptidic compounds of this invention can also be prepared starting from mono-peptidic compound IC prepared in accordance with the procedures of scheme 1. In this approach, the mono-peptidic compound IC is reacted sequentially with amino protected amino acid to form first the di-peptidic compound ID and then reacting again with another amino protected amino acid to form the tri-peptidic compound IB.

In another aspect of this invention, a specific disease, a disorder or a condition that can be treated with the compound of formula I of this invention include, without any limitation: depression, bipolar disorders, anxiety disorders, psychiatric symptoms, cognitive impairment or memory disorders, and schizophrenia. Again, in this embodiment of the invention the compound of formula I as described herein includes enantiomers, stereoisomers, and tautomers of said compound and pharmaceutically acceptable salts, solvates or derivatives thereof.

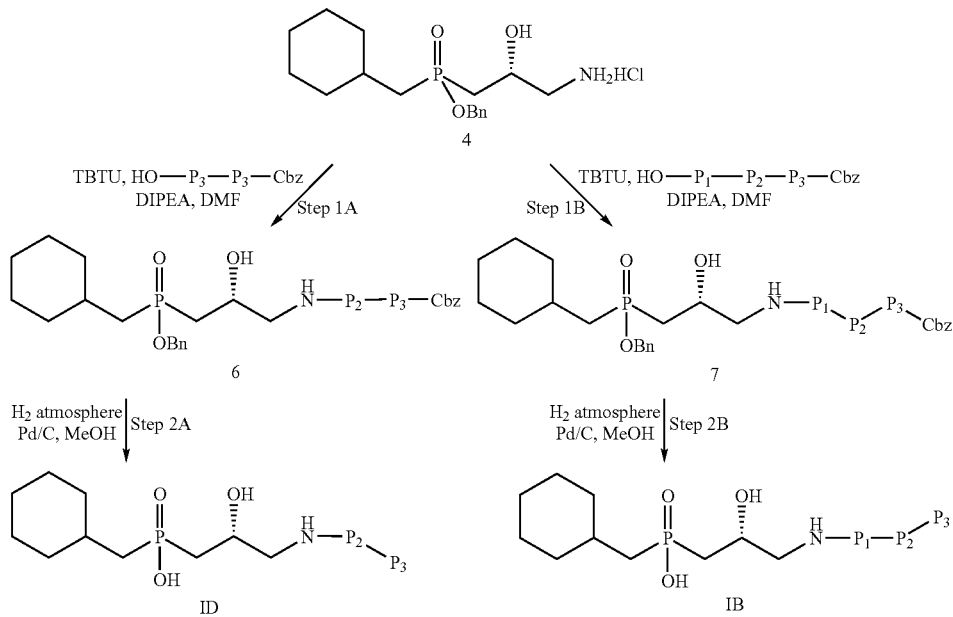

In Step 1A, Scheme 2, compound 4 is reacted with suitably N-amino-protected dipeptide. This reaction is carried out in an analogous manner as described in Step 4 of Scheme 1 Thus, for instance, a di-peptide protected with benzyloxycarbonyl group at the amino end (HO-$P_2$-$P_3$-Cbz) is reacted with compound 4 in the presence of TBTU and DIPEA in the presence of a suitable organic solvent such as DMF. This results in amino-protected di-peptidic compound 6, which is subjected to suitable amino and hydroxy deprotection reaction in Step 2A to afford di-peptidic compounds of this invention, ID, in which $P_1$ is a bond. The deprotection reaction can generally be carried out under hydrogenation conditions as described above. Generally, the resulting compounds may be a mixture of stereoisomers, which can be separated by any of the methods known in the art such as by chromatographic techniques as further discussed in greater detail in the specific examples that are provided below. In an analogous manner, starting from a suitable amino protected tri-peptide, tri-pep- One of skill in the art readily appreciates that the pathologies and disease states expressly stated herein are not intended to be limiting rather to illustrate the efficacy of the compounds of the present invention. Thus it is to be understood that the compounds of this invention may be used to treat any disease caused by the effects of γ-aminobutyric acid (GABA). That is, the active metabolite of the compounds of the present invention is a $GABA_B$ antagonist and thus compounds of this invention may be effectively administered to ameliorate any disease state which is mediated all or in part by the $GABA_B$ antagonist.

In one of the preferred embodiments of this invention the compounds of this invention are particularly suitable for treating depression. Various types of depressive disorders that can be treated by the compounds of this invention include without any limitation are the following: major depressive episode, dysthymia, melancholia, seasonal affective disorders and depression arising from pre-menstrual tension and adolescence.

A feature of depression or depressive disorders ("unipolar depression") is one or more major depressive episodes without a history of manic, mixed, or hypomanic episodes. See, Diagnostic and Statistical Manual of Mental Disorders, 4$^{th}$ Ed., ("DSM-IV") American Psychiatric Association, 1995, incorporated herein by reference. Each of the sub-classes of depressive disorders is differentiated by symptoms exhibited by a patient. For instance, a major depressive disorder is characterized by one or more major depressive episodes (i.e., at least two weeks of depressed mood or loss of interest accompanied by at least four additional symptoms of depression). Whereas dysthymia or dysthymic disorder is characterized by at least two years of depressed mood for more days than not, accompanied by additional depressive symptoms that do not meet criteria for a major depressive episode. Thus, dysthymic disorder and major depressive disorder are differentiated based on severity, chronicity, and persistence. In major depressive disorder, the depressive mood must be present for most of the day, nearly every day, for a period of at least two weeks, whereas dysthymic disorder must be present for more days than not over a period of at least two years.

A melancholic feature is loss of interest or pleasure in all, or almost all, activities or a lack of reactivity to usually pleasurable stimuli. The individual's depressed mood does not improve, even temporarily, when something good happens. In addition, at least three of the following symptoms are present: a distinct quality of the depressed mood, depression that is regularly worst in the morning, early morning awakening, psychomotor retardation or agitation, significant anorexia or weight loss, or excessive or inappropriate guilt.

A feature of the seasonal affective disorders is the onset and remission of major depressive episodes at characteristic times of the year. In most cases, the episodes begin in fall or winter and remit in spring. Less commonly, there may be recurrent summer depressive episodes. See, DSM-IV or E. M. Tam et al., Can. J. Psychiatry 1995, 40, 457-466.

Bipolar disorders are further classified into four sub-categories: bipolar I disorder, bipolar II disorder, cyclothymic disorder and bipolar disorder not otherwise specified. Generally, bipolar disorders involve the presence (or history) of manic episodes, mixed episodes, or hypomanic episodes, usually accompanied by the presence (or history) of major depressive episodes. Bipolar I disorder is characterized by one or more manic or mixed episodes, usually accompanied by major depressive episodes. Bipolar II disorder is characterized by one or more major depressive episodes accompanied by at least one hypomanic episode. Cyclothymic disorder is characterized by at least two years of numerous periods of hypomanic symptoms that do not meet criteria for a manic episode and numerous periods of depressive symptoms that do not meet criteria for a major depressive episode.

In another aspect of this invention, the compounds of this invention are particularly useful in the treatment of a variety of anxiety disorders. Various types of anxiety disorders that can be treated without any limitation include the following: panic attack, social phobia, obsessive compulsive disorder, posttraumatic stress disorder and generalized anxiety disorder.

A panic attack or a panic disorder is a discrete period in which there is the sudden onset of intense apprehension, fearfulness, or terror, often associated with feelings of impending doom. During these attacks, symptoms such as shortness of breath, palpitations, chest pain or discomfort, choking or smothering sensations, and fear of "going crazy" or losing control are present.

Social phobia or social anxiety disorder is characterized by clinically significant anxiety provoked by exposure to certain types of social performance situations, often leading to avoidance behavior.

Obsessive compulsive disorder is characterized by obsessions (which cause marked anxiety or distress) and/or by compulsions (which serve to neutralize anxiety).

Posttraumatic stress disorder is characterized by the reexperiencing of an extremely traumatic event accompanied by symptoms of increased arousal and by avoidance of stimuli associated with the trauma.

Generalized anxiety disorder is characterized by at least six months of persistent and excessive anxiety and worry.

In a further aspect of the method of this invention, the compounds of formula I are particularly useful in treating psychiatric symptoms. Various psychiatric symptoms that can be treated by the compounds of this invention include without any limitation the following: anger, rejection sensitivity and lack of mental or physical energy.

In a further aspect of this embodiment of the invention, the compounds of this invention can also be used to treat psychiatric symptoms that are associated with premenstrual disorders. Specific psychiatric symptoms associated with menstrual disorders are selected from the group consisting of: anger, rejection sensitivity and lack of mental or physical energy.

Cognitive impairment or memory disorders is characterized by "memory loss", i.e., any disruption related to learning and memory. A "disruption relating to learning and memory" refers to any impairment associated with memory formation and/or memory recall. "Memory" can be, for example, short-term memory, long-term memory, explicit memory, i.e., memory for a conscious fact, e.g., the memory of a specific, event, or implicit or procedural memory, i.e., memory relating to an "unconsciously" performed task, e.g., riding a bicycle.

"Schizophrenia" is a disturbance that lasts for at least six months and includes at least one month of active-phase symptoms. That is, two or more of the following: delusions, hallucinations, disorganized speech, grossly disorganized speech, grossly disorganized or catatonic behavior and negative symptoms. The compounds of this invention can also be used to treat a variety of subtypes of schizophrenia. Various subtypes of schizophrenia and their definitions are set forth below.

Schizophreniform disorder is characterized by a symptomatic presentation that is equivalent to schizophrenia except for its duration (i.e., the disturbance lasts from one to six months) and the absence of a requirement that there be a decline in functioning.

Schizoaffective disorder is a disturbance in which a mood episode and the active-phase symptoms of schizophrenia occur together and were preceded or are followed by at least two weeks of delusions or hallucinations without prominent mood symptoms.

Delusional disorder is characterized by at least one month of nonbizarre delusions without other active-phase symptoms of schizophrenia.

Brief psychotic disorder is a psychotic disturbance that lasts more than one day and remits by one month.

Shared psychotic disorder is a disturbance that develops in an individual who is influenced by someone else who has an established delusion with similar content.

In psychotic disorder due to a general medical condition, the psychotic symptoms are judged to be a direct physiological consequence of a general medical condition.

In substance-induced psychotic disorder, the psychotic symptoms are judged to be a direct physiological consequence of a drug of abuse, a medication, or toxin exposure.

There are many ways to show that the compounds of the present invention are useful in treating various diseases as described herein, such as in animal models. See for example, "Animal Models as Simulations of Depression" by Paul Willner, *TiPS* 12:131-136 (April 1991); "Animal Models of Depression: An overview" by Paul Willner, *Pharmac. Ther.* 45:425-455 (1990), both of which are incorporated herein by reference. One such model to show efficacy of the compounds of this invention in treating depression is the chronic mild stress model of depression ("CMS").

CMS uses mild stressors, such as food and water deprivation, cage tilts, changes of cage mates, etc. Over a period of weeks of exposure to the mild stressors, the animals gradually reduce their consumption of a highly preferred sucrose solution which persists (in untreated animals) for several weeks following the cessation of stress. This decreased sensitivity to reward (the sucrose solution) reflects anhedonia, a symptom of a major depressive episode (see for example, Behavioral Pharmacol. 5: Suppl. 1, p. 86 (1994) where lithium, carbamazepine and ketoconazole were evaluated in CMS; Psychopharmacology 93:358-364 (1987) where a tricyclic antidepressant was evaluated in CMS; Behavioral Pharmacology: 5:344-350 (1994) where a catechol-O-methyl transferase inhibitor was evaluated in CMS).

Similarly, suitable other in vivo animal models that can be used to show the efficacy of the compounds of this invention in treating depression include forced swim test and/or social conflict test. The latter test can also be used to show the efficacy of the compounds of this invention in treating certain anxiety disorders. Another animal model to show the efficacy of the compounds of this invention in treating anxiety disorder is a social phobia test.

Object recognition test is another commonly used animal model to test the efficacy of the compounds in treating diseases involving various cognition impairment. See, for example Ennaceur et al., Behav. Brain Res., 1988, 31, 47-59. The test is based on the spontaneous exploratory activity of the animal and has the characteristics of episodic memory in humans. This memory test is sensitive to ageing (Scali et al., Eur. J. Pharmacol., 1997, 325, 173-180) and to cholinergic dysfunctions (Bartolini et al., Pharm. Biochem. Behav. 1996, 53(2), 277-283) and is based on the differences in the exploration of two objects of fairly similar shape-one familiar, the other new.

Of course, clinical trials on humans may also be used to show the usefulness of the compounds of the present invention in treating depression such as using the abbreviated Hamilton Psychiatric Rating Scale for depression. This comprises a series of 17 categories in which the individual is rated, e.g., for depressed mood, guilt, suicide tendencies, insomnia, anxiety, etc., to reach a score which indicates to the clinician whether or not the patient is suffering depression.

Finally, various preferred embodiments of compounds of formula IB, IC or ID as described herein can be used in treating various diseases as discussed herein. That is, various mono-peptides, di-peptides and tripeptides of this invention including the preferred embodiments of these compounds can be used in the method of this invention.

In another embodiment of the method of this invention, the compounds of this invention can be administered by any of the methods known in the art. Specifically, the compounds of this invention can be administered by oral, intramuscular, subcutaneous, rectal, intratracheal, intranasal, intraperitoneal or topical route. More preferably, the compounds of this invention are administered by an oral route.

Finally, in yet another embodiment of this invention, there is also provided a pharmaceutical composition comprising a pharmaceutically acceptable carrier and a compound, including enantiomers, stereoisomers, and tautomers of said compound and pharmaceutically acceptable salts, solvates or derivatives thereof, with said compound having the general structure shown in formula I as described herein.

As described herein, the pharmaceutical compositions of this invention feature $GABA_B$ antagonist activity and thus are useful in treating any disease, condition or a disorder caused due to the effects of $GABA_B$ in a patient. Again, as described above, all of the preferred embodiments of the compounds of this invention as disclosed herein can be used in preparing the pharmaceutical compositions as described herein.

Preferably the pharmaceutical compositions of this invention are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Flavored unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

The pharmaceutical compositions of this invention can be administered by any of the methods known in the art. In general, the pharmaceutical compositions of this invention can be administered by oral, intramuscular, subcutaneous, rectal, intratracheal, intranasal, intraperitoneal or topical route. The preferred administration of the pharmaceutical composition of this invention is by an oral route. Any of the known methods to administer pharmaceutical compositions by an oral route can be used to administer the composition of this invention.

In the treatment of various disease states as described herein, a suitable dosage level is about 0.01 to 250 mg/kg per day, preferably about 0.05 to 100 mg/kg per day, and especially about 0.05 to 20 mg/kg per day. The compounds may be administered on a regimen of 1 to 4 times per day.

This invention is further illustrated by the following examples which are provided for illustration purposes and in no way limit the scope of the present invention.

EXAMPLES

General

Unless otherwise stated, the reactions generally are run under a nitrogen atmosphere. Solvents are dried over magnesium sulfate ($MgSO_4$) and are evaporated under vacuum on a rotary evaporator. Gradient flash chromatography is performed using RediSep disposable column. The $^1H$ NMR and $^{31}P$ NMR spectra are run at 300 MHz on a Gemini 300 or Varian VXR 300 spectrometer and are determined in a deuterated solvent, such as $CD_3OD$ or $CDCl_3$ unless otherwise noted. Chemical shifts values are indicated in parts per million (ppm) with reference to tetramethylsilane (TMS) as the internal standard for $^1H$ NMR. The LCMS are run on a Micromass Platform LCZ.

As used in the examples and preparations that follow, the terms used therein shall have the meanings indicated: "kg" refers to kilograms, "g" refers to grams, "mg" refers to milligrams, "µg" refers to micrograms, "mol" refers to moles, "mmol" refers to millimoles, "µmole" refers to micromoles, "nmole" refers to nanomoles, "L" refers to liters, "mL" refers to milliliters, "µL" refers to microliters, "° C." refers to degrees Celsius, "conc." refers to concentrated, "psi" refers to pounds per square inch, "THF" refers to tetrahydrofuran, "DMF" refers to dimethylformamide, "MeCN" or "$CH_3CN$" refers to acetonitrile, "EtOAc" refers to ethyl acetate, "$CH_2Cl_2$" refers to methylene chloride, "MeOH" refers to methanol, "NaOH" refers to sodium hydroxide, "HCl" refers to hydrochloric acid, "Pd/C" refers to palladium on carbon, "HOBT" refers to hydroxybenzotriazole, "EEDQ" refers to 1-ethoxycarbonyl-2-ethoxy-1,2-dihydroquinoline, "TBTU" refers to 2-(1H-benzotriazol-1-yl)-1,1,3,3-tetramethyluronium tetrafluoroborate, "HATU" refers to O-(7-azabenzotriazol-1-yl)-1,1,3,3-tetramethyluronium hexafluorophosphate, "Boc" refers to tert-butyloxycarbonyl, "Bn" refers to benzyl, "Cbz" or "Z" refers to benzyloxycarbonyl, "brine" refers to a saturated aqueous sodium chloride solution, "M" refers to molar, "mM" refers to millimolar, "µM" refers to micromolar, "nM" refers to nanomolar, "N" refers to normal, "HPLC" refers to high performance liquid chromatography, "RP-HPLC" refers to reverse phase high performance liquid chromatography, "i.p." refers to intraperitoneally, "i.v." refers to intravenously, "anhyd" refers to anhydrous, "aq" refers to aqueous, "min" refers to minute, "h" or "hr" refers to hour, "d" refers to day, "sat." refers to saturated, "s" denotes singlet, "d" denotes doublet, "t" denotes triplet, "q" denotes quartet, "m" denotes multiplet, "dd" denotes doublet of doublets, "br" denotes broad, "LC" refers to liquid chromatograph, "MS" refers to mass spectrograph, "M" refers to molecular ion.

The following examples describe the procedures used for the preparation of various starting materials employed in the preparation of the compounds of this invention.

Example 1

[(R)-3-((S)-2-Amino-3-methyl-butyrylamino)-2-hydroxy-propyl]-cyclohexylmethyl-phosphinic acid

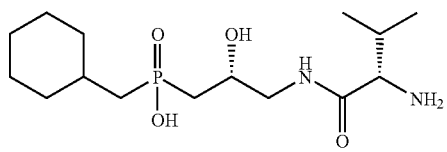

Step 1: ((R)-3-tert-Butoxycarbonylamino-2-hydroxy-propyl)-cyclohexylmethyl-phosphinic acid: To a stirred solution of ((R)-3-amino-2-hydroxy-propyl)-cyclohexylmethyl-phosphinic acid (20.2 g, 86 mmol) dissolved in an aqueous solution of potassium carbonate (35.6 g, 258 mmol in 270 mL of water) was slowly added a solution of di-t-butyl-dicarbonate (24.36 g, 112 mmol) in THF (90 mL) at room temperature. The reaction mixture was continued to stir at room temperature for 4 hours, after which time ethyl acetate (200 mL) was added. The aqueous phase was separated and was washed with ethyl acetate (200 mL) before carefully acidifying with 1N HCl (~450 mL) to pH=2. Extraction into ethyl acetate (500 mL total), and drying ($MgSO_4$) gave a clear, colorless solution. Product began to crystallize from this solution upon standing. The total volume was reduced to ~150 mL (in vacuo) before adding heptane (300 mL). The solution was left at room temperature for 30 minutes to cool and crystallize. The solid product was collected, washed with 30% ethyl acetate/heptane (2×100 mL), and dried under high vacuum. ((R)-3-tert-Butoxycarbonylamino-2-hydroxy-propyl)-cyclohexylmethyl-phosphinic acid (26.54 g, 92%) was isolated as colorless needles. $^1H$ NMR ($CDCl_3$, 300 MHz): δ 4.75 (s, 1H), 4.18 (br s, 1H), 3.4-3.24 (m, 1H), 3.21-3.09 (m, 1H), 2.01-1.58 (m, 10H), 1.43 (s, 9H), 1.37-0.95 (m, 6H). LCMS m/z: [M+H]$^+$=336.4.

Step 2: ((R)-3-tert-Butoxycarbonylamino-2-hydroxy-propyl)-cyclohexylmethyl-phosphinic acid benzyl ester: ((R)-3-tert-Butoxycarbonylamino-2-hydroxy-propyl)-cyclohexyl-methyl-phosphinic acid (8.0 g, 23.8 mmol) was dissolved in a solution of potassium carbonate (3.3 g, 23.8 mmol) and water (33 mL) and stirred with gentle warming. The water was removed in vacuo and the residue dried under vacuum for 24 hours at 75° C. in the presence of phosphorous pentoxide to give the potassium salt as a white solid. To the potassium salt under a nitrogen atmosphere was added acetonitrile (200 mL), benzylbromide (4.08 g, 23.8 mmol) and 18-crown-6 (0.03 g, 0.120 mmol), and the mixture refluxed overnight at 80° C., with stirring. The reaction was cooled to room temperature, filtered and the filtrate concentrated in vacuo to give the crude product as a foam (10.2 g). The crude product was purified by gradient flash chromatography (25% ethyl acetate/methylene chloride to 100% ethyl acetate) to give the title compound as a white solid (6.43 g, 15.05 mmol). $^1H$ NMR (CDCl₃, 300 MHz): δ 7.42-7.31 (m, 5H), 5.05 (t, 3H), 4.48-4.40 (m, 1H), 4.18-4.02 (m, 1H), 3.42-3.22 (m, 1H), 3.20-3.04 (m, 1H), 2.01-1.58 (m, 10H), 1.48 (s, 9H), 1.40-0.95 (m, 5H). LCMS m/z: [M+H]⁺=426.2.

Step 3: ((R)-3-Amino-2-hydroxy-propyl)-cyclohexylmethyl-phosphinic acid benzyl ester hydrochloride: ((R)-3-tert-Butoxycarbonylamino-2-hydroxy-propyl)-cyclohexylmethyl-phosphinic acid benzyl ester (6 g, 14.05 mmol) was dissolved in ethyl acetate (200 mL) and cooled in an ice bath with stirring. HCl gas was bubbled into the solution via a pipette at a controlled rate such that the temperature of the reaction mixture was maintained at about 10° C. After saturation, the reaction mixture was stirred at about 0° C. and the progress of the reaction was monitored by HPLC. Upon completion (3-4 hours) the reaction mixture was concentrated in vacuo at room temperature and the residue was placed under high vacuum for a few hours to afford a sticky foam, this material was used as such in the next step. ¹H NMR (CDCl₃, 300 MHz): δ 8.26 (br s, 3H), 7.51-7.23 (m, 5H), 5.38-4.93 (br. m, 3H), 4.58 (br. s, 1H), 3.48-3.03 (m, 2H), 2.40-2.02 (m, 2H), 1.98-1.52 (m, 8H), 1.38-0.85 (m, 5H). LCMS m/z: [M+H]⁺=326.1.

Step 4: [(R)-3-((S)-2-Benzyloxycarbonylamino-3-methyl-butyrylamino)-2-hydroxy-propyl]-cyclohexylmethyl-phosphinic acid benzyl ester: The title compound can be synthesized in accordance with any one of the four procedures set forth below.

Method A: A flask was charged with N-Cbz-L-valine (1.02 g, 4.04 mmol) and DMF (60 mL) and stirred under nitrogen. To this was added diisopropylethylamine (2.11 mL, 12.1 mmol) followed by TBTU (1.30 g, 4.04 mmol). After stirring for 5 minutes, a solution of ((R)-3-amino-2-hydroxy-propyl)-cyclohexylmethyl-phosphinic acid benzyl ester hydrochloride (8.08 mmol) dissolved in DMF (10 mL) was added. The reaction mixture was stirred overnight at room temperature. The reaction was diluted with ethyl acetate (300 mL) and the organic layer washed with 1N HCl (2×100 mL), water (100 mL), saturated sodium bicarbonate solution (2×100 mL) and brine (100 mL). The organic layer was dried over sodium sulfate, filtered and concentrated in vacuo to give the crude product as an amber oil. The crude product was purified by gradient flash chromatography (methanol/methylene chloride) on a 120 g RediSep disposable column to give (1.10 g, 1.97 mmol) of [(R)-3-((S)-2-benzyloxycarbonylamino-3-methyl-butyrylamino)-2-hydroxy-propyl]-cyclohexylmethyl-phosphinic acid benzyl ester as a white foam. ¹H NMR (CDCl₃, 300 MHz): δ 7.40-7.25 (m, 10H), 6.70-6.51 (m, 1H), 5.48-5.35 (m, 1H), 5.18-5.01 (m, 4H), 4.20-3.98 (m, 2H), 3.62-3.42 (m, 1H), 3.38-3.18 (m, 1H), 2.30-2.05 (m, 1H), 2.03-1.60 (m, 10H, 1.38-1.02 (m, 5H), 0.98 (dd, 6H). LCMS m/z: [M+H]⁺=559.

Method B: ((R)-3-Amino-2-hydroxy-propyl)-cyclohexylmethyl-phosphinic acid benzyl ester hydrochloride (2.10 mmol) was dissolved in DMF (30 mL) under nitrogen and stirred at 0° C. To this was added sequentially hydroxybenzotriazole (0.91 g, 6.72 mmol), N-Cbz-L-valine (0.63 g, 2.52 mmol), triethylamine (0.58 mL, 4.2 mmol) followed by 1-(3-dimethylaminopropyl)-3-ethylcarbodiimide hydrochloride (0.48 g, 2.52 mmol). The stirred reaction mixture was allowed to warm to room temperature and continued to stir overnight. The reaction was diluted with ethyl acetate (300 mL) and was washed with brine (100 mL). The brine layer was back extracted with ethyl acetate (2×100 mL) and the organic fractions were combined and were washed with 10% citric acid (2×100 mL), saturated sodium bicarbonate solution (2×100 mL) and brine (100 mL). The organic layer was dried over sodium sulfate, filtered and concentrated in vacuo to give the crude product which was purified by flash chromatography (as in Method A) to give (0.72 g, 1.29 mmol) of [(R)-3-((S)-2-benzyloxycarbonylamino-3-methyl-butyrylamino)-2-hydroxy-propyl]-cyclohexylmethyl-phosphinic acid benzyl ester as a white foam. NMR and MS spectra were substantially similar to the product obtained via Method A set forth above.

Method C: To a solution of N-Cbz-L-valine (1.0 g, 3.98 mmol) dissolved in CH₂Cl₂ (80 mL) under nitrogen was added hydroxybenzotriazole (0.538 g, 3.98 mmol) and PS-Carbodiimide (2.25 g, 5.17 mmol). After stirring for 10 min, triethylamine (0.665 mL, 4.78 mmol) and ((R)-3-amino-2-hydroxy-propyl)-cyclohexylmethyl-phosphinic acid benzyl ester hydrochloride (1.44 g, 3.98 mmol) were added. The reaction was stirred for 2 h, then filtered and concentrated in vacuo. The residue was purified by flash chromatography with methanol/dichloromethane on a 35 g RediSep disposable column to give [(R)-3-((S)-2-benzyloxycarbonylamino-3-methyl-butyrylamino)-2-hydroxy-propyl]-cyclohexylmethyl-phosphinic acid benzyl ester (0.60 g, 1.07 mmol) as a white foam. NMR and MS spectra were substantially similar to the product obtained via Method A set forth above.

Method D: To a stirred solution of N-Cbz-L-valine (1 g, 4 mmol) in dichloromethane (20 mL) and DMF (1 mL) was added diisopropylethylamine (1.05 g, 8 mmol) and HATU (1.6 g, 4.2 mmol). After stirring for 15 minutes, a solution of ((R)-3-amino-2-hydroxy-propyl)-cyclohexylmethyl-phosphinic acid benzyl ester hydrochloride (1.45 g, 4 mmol) and diisopropylethylamine (1.05 g, 8 mmol) dissolved in dichloromethane (20 mL) and DMF (3 mL) was added to the reaction mixture and left stirring at room temperature overnight. The reaction mixture was diluted with EtOAc (100 mL) and the organic phase was washed with 1N HCl (3×100 mL), 1N NaOH (3×100 mL), and brine (100 mL). The organic layer was dried over magnesium sulfate, filtered and concentrated in vacuo to give the crude residue which was purified by column chromatography on a prepacked silica gel column with gradient dilution from neat dichloromethane to 4% MeOH/CH₂Cl₂. Pure fractions were combined and concentrated to dryness, to give a white foamy solid. NMR and MS spectra were substantially similar to the product obtained via Method A set forth above.

Step 5: [(R)-3-((S)-2-Amino-3-methyl-butyrylamino)-2-hydroxy-propyl]-cyclohexylmethyl-phosphinic acid: The title compound can be synthesized in accordance with any one of the two procedures set forth below.

Method A: [3-(2-Benzyloxycarbonylamino-3-methyl-butyrylamino)-2-hydroxy-propyl]-cyclohexylmethyl-phosphinic acid benzyl ester (5.20 g, 9.32 mmol) was dissolved in methanol (200 mL) and hydrogenated overnight via a hydrogen balloon with 10% Pd/C (0.52 g) as a catalyst. The reaction was filtered through celite and concentrated in vacuo to give a white foam. The residue was taken up in water and concentrated in vacuo to dryness to give the title compound (3.15 g, 9.32 mmol) as a white crystalline solid. ¹H NMR (CD₃OD, 300 MHz): δ 4.18-4.01 (m, 1H), 3.61 (d, 1H), 3.43 (dd, 1H), 3.35-3.22 (m, 1H), 2.30-2.08 (m, 1H), 1.95 (br.d, 2H), 1.82-1.58 (m, 6H), 1.53 (dd, 2H), 1.42-1.05 (m, 3H), 1.08 (d, 6H), 1.07-0.98 (m, 2H). LCMS m/z: [M+H]⁺=335.19. ³¹P NMR (CD₃OD, 300 MHz): δ 40.51.

Method B: [3-(2-Benzyloxycarbonylamino-3-methyl-butyrylamino)-2-hydroxy-propyl]-cyclohexylmethyl-phosphinic acid benzyl ester (1.3 g, 2.33 mmol) was dissolved in ethanol (50 mL) and was hydrogenated via a hydrogen par shaker for 2 h at 50 psi with 10% Pd/C (0.35 g) as a catalyst. The reaction was filtered through celite and concentrated in vacuo to give a white foam. The residue was purified by RP-HPLC eluting with a gradient of 10% CH₃CN/H₂O (adjusted with HCl to pH=3.5) to 100% CH₃CN. The appropriate fractions were combined and were lyophilized to give the title compound (0.66 g, 1.97 mmol) as a white solid. NMR and MS spectra were substantially similar to the product obtained via Method A set forth above.

Example 2

[(R)-3-(2-Amino-acetylamino)-2-hydroxy-propyl]-cyclohexylmethyl-phosphinic acid

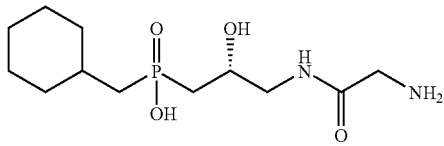

Step 4, Method B of Example 1 was substantially repeated in this Example 2 except for employing ((R)-3-amino-2-hydroxy-propyl)-cyclohexylmethyl-phosphinic acid benzyl ester hydrochloride and N-Cbz-glycine as the starting materials. Subsequent hydrogenation of the resulting benzyl ester in accordance with the procedures of Step 5, Method A of Example 1 yielded the title compound. ¹H NMR (CD₃OD, 300 MHz): δ 4.18-4.01 (m, 1H), 3.85 (s, 2H), 3.55-3.40 (m, 1H), 3.38-3.22 (m, 1H), 1.91-1.40 (m, 10H), 1.38-0.90 (m, 5H). ³¹P NMR (CD₃OD, 300 MHz): δ 39.92. LCMS m/z: [M+H]⁺=293.1.

Example 3

[(R)-3-((S)-2-Amino-propionylamino)-2-hydroxy-propyl]-cyclohexylmethyl-phosphinic acid

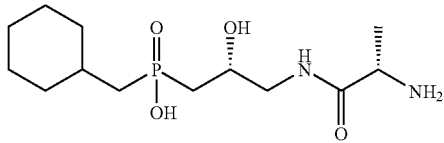

Step 4, Method B of Example 1 was substantially repeated in this Example 3 except for employing ((R)-3-amino-2-hydroxy-propyl)-cyclohexylmethyl-phosphinic acid benzyl ester hydrochloride and N-Cbz-L-alanine as the starting materials. Subsequent hydrogenation of the resulting benzyl ester in accordance with the procedures of Step 5, Method A of Example 1 and RP-HPLC purification yielded the title compound. ¹H NMR (CD₃OD, 300 MHz): δ 4.18-3.99 (m, 1H), 3.93 (q, 1H), 3.42-3.25 (m, 2H), 1.98-1.85 (m, 2H), 1.83-1.61 (m, 6H), 1.59-1.55 (m, 2H), 1.52 (d, 3H), 1.42-0.98 (m, 5H). ³¹P NMR (CD₃OD, 300 MHz): δ 42.98. LCMS m/z: [M+H]⁺=307.2.

Example 4

[(R)-3-((R)-2-Amino-3-methyl-butyrylamino)-2-hydroxy-propyl]-cyclohexylmethyl-phosphinic acid

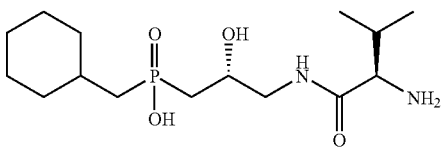

Step 4, Method B of Example 1 was substantially repeated in this Example 4 except for employing ((R)-3-amino-2-hydroxy-propyl)-cyclohexylmethyl-phosphinic acid benzyl ester hydrochloride and N-Cbz-D-valine as the starting materials. Subsequent hydrogenation of the resulting benzyl ester in accordance with the procedures of Step 5, Method A of Example 1 yielded the title compound. ¹H NMR (CD₃OD, 300 MHz): δ 4.15-4.01 (m, 1H), 3.58 (d, 1H), 3.55-3.43 (m, 1H), 3.32-3.15 (m, 1H), 2.25-2.07 (m, 1H), 2.02-1.85 (m, 2H), 1.83-1.58 (m, 6H), 1.56-1.45 (m, 2H), 1.42-1.18 (m, 3H), 1.10 (d, 6H), 1.08-0.96 (m, 2H). ³¹P NMR (CD₃OD, 300 MHz): δ 40.91. LCMS m/z: [M+H]⁺=335.1.

Example 5

[(R)-3-((S)-2-Amino-4-methyl-pentanoylamino)-2-hydroxy-propyl]-cyclohexylmethyl-phosphinic acid

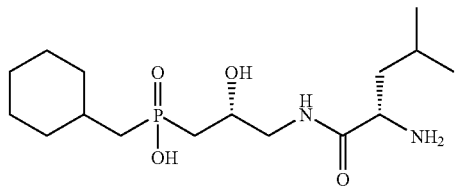

Step 4, Method B of Example 1 was substantially repeated in this Example 5 except for employing ((R)-3-amino-2-hydroxy-propyl)-cyclohexylmethyl-phosphinic acid benzyl ester hydrochloride and N-Cbz-L-leucine as the starting materials. Subsequent hydrogenation of the resulting benzyl ester in accordance with the procedures of Step 5, Method A of Example 1 yielded the title compound. ¹H NMR (CD₃OD, 300 MHz): δ 4.18-3.98 (m, 1H), 3.83 (t, 1H), 3.52-3.38 (m, 1H), 3.35-3.20 (m, 1H), 1.95 (br d, 2H), 1.83-1.58 (m, 9H), 1.52 (dd, 2H), 1.42-1.15 (m, 3H), 1.10-0.95 (m, 8H). ³¹P NMR (CD₃OD, 300 MHz): δ 41. LCMS m/z: [M+H]⁺=349.2.

Example 6

[(R)-3-((S)-2-Amino-3-methyl-pentanoylamino)-2-hydroxy-propyl]-cyclohexylmethyl-phosphinic acid

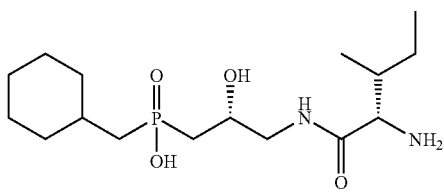

Step 4, Method B of Example 1 was substantially repeated in this Example 6 except for employing ((R)-3-amino-2-hydroxy-propyl)-cyclohexylmethyl-phosphinic acid benzyl ester hydrochloride and N-Cbz-L-isoleucine as the starting materials. Subsequent hydrogenation of the resulting benzyl ester in accordance with the procedures of Step 5, Method A of Example 1 and RP-HPLC purification yielded the title compound. $^1$H NMR (CD$_3$OD, 300 MHz): δ 4.18-4.03 (m, 1H), 3.72 (d, 1H), 3.40-3.35 (m, 2H), 2.01-1.85 (m, 5H), 1.80-1.50 (m, 7H), 1.42-1.18 (m, 4H), 1.17-0.95 (m, 8H). $^{31}$P NMR (CD$_3$OD, 300 MHz): δ 53.18. LCMS m/z: [M+H]$^+$=349.2.

Example 7

Cyclohexylmethyl-{(R)-2-hydroxy-3-[((S)-pyrrolidine-2-carbonyl)-amino]-propyl}-phosphinic acid

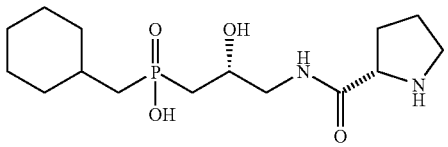

Step 4, Method B of Example 1 was substantially repeated in this Example 7 except for employing ((R)-3-amino-2-hydroxy-propyl)-cyclohexylmethyl-phosphinic acid benzyl ester hydrochloride and N-Cbz-L-proline as the starting materials. Subsequent hydrogenation of the resulting benzyl ester in accordance with the procedures of Step 5, Method A of Example 1 and RP-HPLC purification yielded the title compound. $^1$H NMR (CD$_3$OD, 300 MHz): δ 4.32-4.18 (m, 1H), 4.13-3.95 (m, 1H), 3.55-3.20 (m, 4H), 2.52-2.35 (m, 1H), 2.15-1.99 (m, 3H), 1.95 (br. d, 2H), 1.80-1.58 (m, 6H), 1.52 (dd, 2H), 1.40-1.15 (m, 3H), 1.13-0.95 (m, 2H). $^{31}$P NMR (CD$_3$OD, 300 MHz): δ 42.01. LCMS m/z: [M+H]$^+$=333.2.

Example 8

[(R)-3-((S)-2-Amino-3-hydroxy-butyrylamino)-2-hydroxy-propyl]-cyclohexylmethyl-phosphinic acid

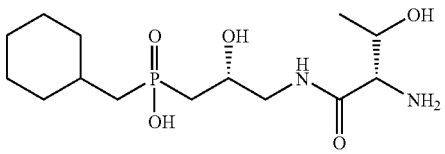

Step 4, Method B of Example 1 was substantially repeated in this Example 8 except for employing ((R)-3-amino-2-hydroxy-propyl)-cyclohexylmethyl-phosphinic acid benzyl ester hydrochloride and N-Cbz-L-threonine-(Bn)-(OH) as the starting materials. Subsequent hydrogenation of the resulting benzyl ester in accordance with the procedures of Step 5, Method A of Example 1 and RP-HPLC purification yielded the title compound. $^1$H NMR (CD$_3$OD, 300 MHz): δ 4.18-3.97 (m, 2H), 3.61 (d, 1H), 3.40-3.30 (m, 2H), 1.92 (br d, 2H), 1.82-1.59 (m, 6H), 1.55 (dd, 2H), 1.40-1.17 (m, 6H), 1.15-0.95 (m, 2H). $^{31}$P NMR (CD$_3$OD, 300 MHz): δ 43.44. LCMS m/z: [M+H]$^+$=337.18.

Example 9

[(R)-3-((S)-2-Amino-3-phenyl-propionylamino)-2-hydroxy-propyl]-cyclohexylmethyl-phosphinic acid trifluoroacetate

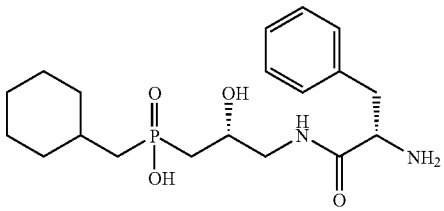

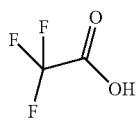

Step 4, Method B of Example 1 was substantially repeated in this Example 9 except for employing ((R)-3-amino-2-hydroxy-propyl)-cyclohexylmethyl-phosphinic acid benzyl ester hydrochloride and N-Cbz-L-phenylalanine as the starting materials. Subsequent hydrogenation of the resulting benzyl ester in accordance with the procedures of Step 5, Method A of Example 1 and RP-HPLC (0.1% TFA buffer) purification yielded the title compound. $^1$H NMR (CD$_3$OD, 300 MHz): δ 7.50-7.21 (m, 5H), 4.20-3.95 (m, 2H), 3.50-3.31 (m, 1H), 3.30-3.18 (m, 2H), 3.16-2.98 (m, 1H), 2.02-1.53 (m, 10H), 1.43-0.98 (m, 5H). LCMS m/z: [M+H]$^+$=383.2.

Examples 10A and 10B

Example 10A

{(R)-3-[(S)-2-((S)-2-Amino-propionylamino)-3-methyl-butyrylamino]-2-hydroxy-propyl}-cyclohexylmethyl-phosphinic acid, and

Example 10B

{(R)-3-[(R)-2-((S)-2-Amino-propionylamino)-3-methyl-butyrylamino]-2-hydroxy-propyl}-cyclohexylmethyl-phosphinic acid Example 10A
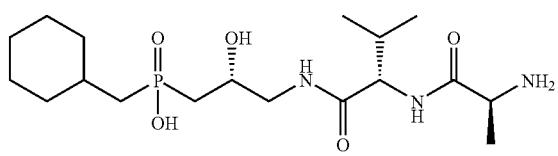

Example 10B
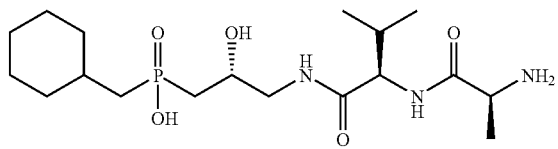

Step 1: {(R)-3-[(S)-2-((S)-2-Benzyloxycarbonylamino-propionylamino)-3-methyl-butyrylamino]-2-hydroxy-propyl}-cyclohexylmethyl-phosphinic acid benzyl ester and {(R)-3-[(R)-2-((S)-2-benzyloxycarbonylamino-propionylamino)-3-methyl-butyrylamino]-2-hydroxy-propyl}-cyclohexylmethyl-phosphinic acid benzyl ester: Diisopropylethylamine (0.54 mL, 3.1 mmol) was added dropwise to a solution of Z-ala-Val-OH (0.50 g, 1.5 mmol) and TBTU (0.523 g, 1.6 mmol) in DMF (5 mL). After 5 min, ((R)-3-amino-2-hydroxy-propyl)-cyclohexylmethyl-phosphinic acid benzyl ester hydrochloride in DMF (2 mL) was added to the reaction mixture and stirred overnight at room temperature under $N_2$. The reaction mixture was diluted with ethyl acetate (100 mL) and washed with half saturated $NaHCO_3$ (2 times), water and brine. The organic layer was dried over $MgSO_4$, filtered and concentrated in vacuo. The residue was purified by $SiO_2$ chromatography using 0-6% $MeOH/CH_2Cl_2$ as the eluent to yield the title diastereomeric mixture (0.686 g, 1.1 mmol) as a glassy solid. $^{31}$P NMR ($CDCl_3$, 300 MHz): δ 59.61, 59.32, 58.31, 58.20. LCMS m/z: [M+H]$^+$=630.23.

Step 2: {(R)-3-[(S)-2-((S)-2-Amino-propionylamino)-3-methyl-butyrylamino]-2-hydroxy-propyl}-cyclohexylmethyl-phosphinic acid and {(R)-3-[(R)-2-((S)-2-amino-propionylamino)-3-methyl-butyrylamino]-2-hydroxy-propyl}-cyclohexylmethyl-phosphinic acid: {(R)-3-[(S)-2-((S)-2-Benzyloxycarbonylamino-propionylamino)-3-methyl-butyrylamino]-2-hydroxy-propyl}-cyclohexylmethyl-phosphinic acid benzyl ester and {(R)-3-[(R)-2-((S)-2-benzyloxycarbonylamino-propionylamino)-3-methyl-butyrylamino]-2-hydroxy-propyl}-cyclohexylmethyl-phosphinic acid benzyl ester (0.686 g, 1.1 mmol) was added to a Paar bottle containing Pd/C (0.20 g) in anhydrous EtOH (25 mL) under $N_2$. The reaction mixture was treated under $H_2$ at 45 psi for 2 hrs then filtered through Celite and concentrated in vacuo. The residue was purified by RP-HPLC using 10-100% $CH_3CN/(HCl/H_2O$, pH=3.5) over 20 min at 45 mL/min. The first fraction was lyophilized to give {(R)-3-[(S)-2-((S)-2-amino-propionylamino)-3-methyl-butyrylamino]-2-hydroxy-propyl}-cyclohexylmethyl-phosphinic acid (0.155 mg) as a white solid and the second fraction was lyophilized to give {(R)-3-[(R)-2-((S)-2-amino-propionylamino)-3-methyl-butyrylamino]-2-hydroxy-propyl}-cyclohexylmethyl-phosphinic acid (0.132 mg) as a white solid. The NMR and MS data for these compounds are set forth below. {(R)-3-[(S)-2-((S)-2-Amino-propionylamino)-3-methyl-butyrylamino]-2-hydroxy-propyl}-cyclohexylmethyl-phosphinic acid—$^1$H NMR ($CD_3OD$, 300 MHz): δ 8.08 (t, 1H), 4.22 (d, J=6.9 Hz, 1H), 4.07 (q, J=6.9 Hz, 1H), 4.02 (m, 1H), 3.44 (dd, J=4.5, 13.5 Hz, 1H), 3.17 (dd, J=6.9, 13.5 Hz, 1H), 2.07 (m, 1H), 1.91 (br d, 2H), 1.70-1.61 (m, 6H), 1.52-1.45 (m, 2H), 1.48 (d, J=6.9 Hz, 3H), 1.33-1.14 (m, 3H), 1.06-1.03 (m, 2H), 1.00 (d, J=4.5 Hz, 3H), 0.98 (d, J=4.5 Hz, 3H). $^{31}$P NMR ($CD_3OD$, 300 MHz): δ 41.64. LCMS m/z: [M+H]$^+$=406.33.

{(R)-3-[(R)-2-((S)-2-amino-propionylamino)-3-methyl-butyrylamino]-2-hydroxy-propyl}-cyclohexylmethyl-phosphinic acid—$^1$H NMR ($CD_3OD$, 300 MHz): δ 8.21 (t, 1H), 4.12 (d, J=6.6 Hz, 1H), 4.00 (q, J=6.9 Hz, 1H), 3.98 (m, 1H), 3.44 (dd, J=4.5, 13.2 Hz, 1H), 3.14 (dd, J=6.9, 13.2 Hz, 1H), 2.21 (m, 1H), 1.91 (br d, 2H), 1.72-1.61 (m, 6H), 1.45 (m, 2H), 1.48 (d, J=6.9 Hz, 3H), 1.34-1.15 (m, 3H), 1.07-1.04 (m, 2H), 0.97 (d, J=2.1 Hz, 3H), 0.95 (d, J=2.1 Hz, 3H). $^{31}$P NMR ($CD_3OD$, 300 MHz): δ 42.27. LCMS m/z: [M+H]$^+$=406.3.

Example 11

{(R)-3-[(S)-2-(2-Amino-acetylamino)-3-methyl-butyrylamino]-2-hydroxy-propyl}-cyclohexylmethyl-phosphinic acid

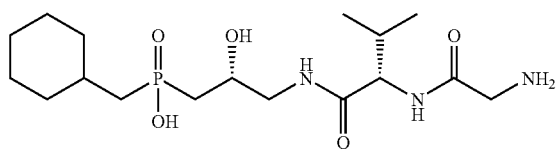

Step 1: [(R)-3-((S)-2-tert-Butoxycarbonylamino-3-methyl-butyrylamino)-2-hydroxy-propyl]-cyclohexylmethyl-phosphinic acid benzyl ester: To a solution of N-Boc-L-valine (1.798 g, 7.15 mmol) and HOBT, (1.257 g, 9.30 mmol) in DMF (10 mL) under $N_2$ was added 1-(3-dimethylaminopropyl)-3-ethylcarbodiimide hydrochloride (1.440 g, 7.51 mmol). The resulting clear solution was stirred at room temperature for 5 min and then a solution of ((R)-3-amino-2-hydroxy-propyl)-cyclohexylmethyl-phosphinic acid benzyl ester hydrochloride (2.589 g, 7.15 mmol) in DMF (15 mL) was added via cannula. Triethylamine (2.0 mL, 14.3 mmol) was added dropwise to the reaction mixture and the resulting solution was stirred overnight at room temperature. The reaction mixture was diluted with ethyl acetate (75 mL) and was washed with saturated $NaHCO_3$, half saturated brine and then brine. The organic layer was dried over $MgSO_4$, filtered and concentrated in vacuo. The residue was purified by $SiO_2$ chromatography using 0-5% $MeOH/CH_2Cl_2$ as the eluent to yield the title diastereomeric compound (2.254 g, 4.296 mmol). $^1H$ NMR ($CD_3OD$, 300 MHz): δ 7.43-7.30 (m, 5H), 5.03 (m, 2H), 4.07 (m, 1H), 3.83-3.80 (m, 1H), 3.34-3.23 (m, 2H), 2.07-1.94 (m, 3H), 1.91-1.75 (m, 5H), 1.69-1.60 (m, 3H), 1.43 (s, 9H), 1.28-1.17 (m, 3H), 1.07-1.00 (m, 2H), 0.94 (d, J=6.6 Hz, 3H), 0.90 (d, J=6.6 Hz, 3H). $^{31}P$ NMR ($CD_3OD$, 300 MHz): δ 61.20, 60.48. LCMS m/z: $[M+H]^+$=525.3.

Step 2: [(R)-3-((S)-2-Amino-3-methyl-butyrylamino)-2-hydroxy-propyl]-cyclohexylmethyl-phosphinic acid benzyl ester hydrochloride: The title compound was prepared essentially following the procedures of Step 3, Example 1 and starting with [(R)-3-((S)-2-tert-butoxycarbonylamino-3-methyl-butyrylamino)-2-hydroxy-propyl]-cyclohexylmethyl-phosphinic acid benzyl ester. The material thus prepared was used in the next step without further purification. $^1H$ NMR ($CD_3OD$, 300 MHz): δ 7.40-7.31 (m, 5H), 5.06-5.00 (m, 2H), 4.09 (m, 1H), 3.62 (d, J=6.0 Hz, 1H), 3.35 (m, 2H), 2.17 (m, 1H), 2.01 (m, 2H), 1.93-1.78 (m, 6H), 1.68 (m, 2H), 1.29-1.18 (m, 3H), 1.07 (m, 2H), 1.06 (d, J=4.5 Hz, 3H), 1.03 (d, J=4.5 Hz, 3H). $^{31}P$ NMR ($CD_3OD$, 300 MHz): δ 60.21, 59.43. LCMS m/z: $[M+H]^+$=425.3.

Step 3: {(R)-3-[(S)-2-(2-Benzyloxycarbonylamino-acetylamino)-3-methyl-butyrylamino]-2-hydroxy-propyl}-cyclohexylmethyl-phosphinic acid benzyl ester: The title compound was prepared substantially in a similar manner as in Step 1 of Example 10 using N-Cbz-glycine and [(R)-3-((S)-2-amino-3-methyl-butyrylamino)-2-hydroxy-propyl]-cyclohexylmethyl-phosphinic acid benzyl ester hydrochloride as the starting materials. The title compound thus obtained was purified by $SiO_2$ chromatography using 0-4% $MeOH/CH_2Cl_2$ as the eluent. $^1H$ NMR ($CD_3OD$, 300 MHz): δ 7.20-7.15 (m, 10H), 5.17 (s, 2H), 5.02 (m, 2H), 4.19 (d, 1H), 4.09 (m, 1H), 3.80 (s, 2H), 3.23-3.15 (m, 2H), 2.08 (m, 1H), 2.01-1.90 (m, 2H), 1.88-1.78 (m, 6H), 1.70-1.59 (m, 2H), 1.30-1.11 (m, 2H), 1.03 (m, 1H), 0.95-0.88 (m, 8H). $^{31}P$ NMR ($CD_3OD$, 300 MHz): δ 60.61, 59.94. LCMS m/z: $[M+H]^+$=616.26.

Step 4: {(R)-3-[(S)-2-(2-Amino-acetylamino)-3-methyl-butyrylamino]-2-hydroxy-propyl}-cyclohexylmethyl-phosphinic acid: The title compound was prepared substantially in a similar manner as in Step 2, Example 10 using {(R)-3-[(S)-2-(2-benzyloxycarbonylamino-acetylamino)-3-methyl-butyrylamino]-2-hydroxy-propyl}-cyclohexylmethyl-phosphinic acid benzyl ester as the starting material. $^1H$ NMR ($CD_3OD$, 300 MHz): δ 4.15 (d, J=6.6 Hz, 1H), 4.00 (m, 1H), 3.74 (q, J=15.9 Hz, 2H), 3.40 (dd, J=5.4, 13.2 Hz, 1H), 3.20 (dd, J=6.0, 13.2 Hz, 1H), 2.13 (m, 1H), 1.91 (br d, 1H), 1.80-1.67 (m, 6H), 1.57 (m, 2H), 1.34-1.15 (m, 3H), 1.09-1.05 (m, 2H), 0.99 (d, J=3.9 Hz, 3H), 0.96 (d, J=3.9 Hz, 3H). $^{31}P$ NMR ($CD_3OD$, 300 MHz): δ 45.26. LCMS m/z: $[M+H]^+$= 392.24.

Examples 12A and 12B

Example 12A

{(R)-3-[(S)-2-((S)-2-Amino-3-methyl-butyrylamino)-4-methyl-pentanoylamino]-2-hydroxy-propyl}-cyclohexylmethyl-phosphinic acid, and Example 12B {(R)-3-[(R)-2-((S)-2-Amino-3-methyl-butyrylamino)-4-methyl-pentanoylamino]-2-hydroxy-propyl}-cyclohexylmethyl-phosphinic acid Example 12A

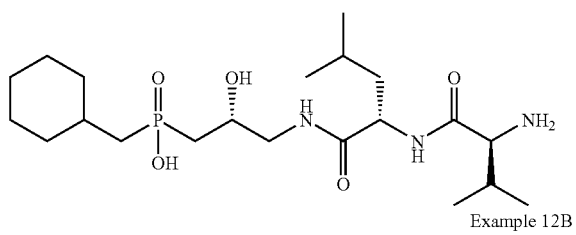

Example 12B

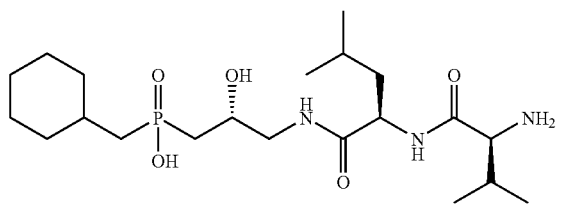

Method A: A flask was charged with N-Cbz-L-valine-L-leucine-OH (0.51 g, 1.4 mmol) and dichloromethane (10 mL) and DMF (1 mL) and stirred under nitrogen. To this was added diisopropylethylamine (0.724 g, 5.6 mmol) followed by TBTU (0.466 g, 1.45 mmol). After stirring for 30 minutes, a solution of ((R)-3-amino-2-hydroxy-propyl)-cyclohexylmethyl-phosphinic acid benzyl ester hydrochloride (8.08 mmol) in dichloromethane (5 mL) and DMF (1 mL) was added. The reaction was stirred overnight at room temperature. The reaction mixture was diluted with ethyl acetate (100 mL) and the organic layer washed with 1N HCl (2×50 mL), 1N NaOH solution (2×50 mL) and brine (50 mL). The organic layer was dried over magnesium sulfate, filtered and concentrated in vacuo to give the crude product. The crude product was purified by gradient flash chromatography (methanol/methylene chloride) on a RediSep disposable column to give (0.553 g, 0.823 mmol) as a diastereomeric mixture of {(R)-3-[(R,S)-2-((S)-2-benzyloxycarbonylamino-3-methyl-butyrylamino)-4-methyl-pentanoylamino]-2-hydroxy-propyl}-cyclohexylmethyl-phosphinic acid benzyl ester. Subsequent hydrogenation of this mixture in accordance with the procedures of Step 5, Method A of Example 1 yielded a mixture of diastereomers. The diastereomers were separated by RP-HPLC using 10-40% $CH_3CN/(HCl/H_2O$, pH=3.5) over 18 min at 70 mL/min. The first fraction was lyophilized to give {(R)-3-[(S)-2-((S)-2-amino-3-methyl-butyrylamino)-4-methyl-pentanoylamino]-2-hydroxy-propyl}-cyclohexylmethyl-phosphinic acid (0.138 g, 0.309 mmol). $^1$H NMR (CD$_3$OD, 300 MHz): δ 4.43-4.34 (m, 1H), 4.10-3.94 (m, 1H), 3.70 (d, 1H), 3.35-3.22 (m, 2H), 2.32-2.15 (m, 1H), 1.93 (br d, 2H), 1.83-1.58 (m, 9H), 1.52 (dd, 2H), 1.40-1.13 (m, 3H), 1.11-0.92 (m, 14H). $^{31}$P NMR (CD$_3$OD, 300 MHz): δ 42.89. LCMS m/z: [M+H]$^+$=448.3. The second fraction gave {(R)-3-[(R)-2-((S)-2-amino-3-methyl-butyrylamino)-4-methyl-pentanoylamino]-2-hydroxy-propyl}-cyclohexylmethyl-phosphinic acid (0.099 g, 0.221 mmol). $^1$H NMR (CD$_3$OD, 300 MHz): δ 4.40-4.32 (m, 1H), 4.08-3.92 (m, 1H), 3.64 (d, 1H), 3.50 (dd, 1H), 3.14 (dd, 1H), 2.21-2.05 (m, 1H), 1.93 (br d, 2H), 1.85-1.60 (m, 9H), 1.52 (dd, 2H), 1.40-1.13 (m, 3H), 1.11-1.00 (m, 8H), 0.97 (d, 3H), 0.92 (d, 3H). $^{31}$P NMR (CD$_3$OD, 300 MHz): δ 42.56. LCMS m/z: [M+H]$^+$=448.3.

Method B: A flask containing ((R)-3-amino-2-hydroxy-propyl)-cyclohexylmethyl-phosphinic acid benzyl ester hydrochloride (1.17 mmol) and a 1:1 mixture of dichloromethane:THF (20 mL) was stirred under nitrogen. To this was added sequentially diisopropylethylamine (0.15 g, 1.17 mmol), N-Cbz-L-valine-L-leucine-OH (0.43 g, 1.17 mmol), and EEDQ (0.49 g, 1.99 mmol) and the reaction stirred for three days. The reaction mixture was concentrated in vacuo and the residue taken up into ethyl acetate (150 mL). The organic layer was washed with 1N HCl (2×50 mL), saturated sodium bicarbonate (2×50 mL), brine (50 mL), dried over sodium sulfate and concentrated in vacuo. The crude product was purified by gradient flash chromatography (methanol/methylene chloride) on a RediSep disposable column to give (0.60 g, 0.890 mmol) of {(R)-3-[(S)-2-((S)-2-benzyloxycarbonylamino-3-methyl-butyrylamino)-4-methyl-pentanoylamino]-2-hydroxy-propyl}-cyclohexylmethyl-phosphinic acid benzyl ester. Subsequent hydrogenation of this benzyl ester in accordance with the procedures of Step 5, Method A of Example 1 yielded {(R)-3-[(S)-2-((S)-2-amino-3-methyl-butyrylamino)-4-methyl-pentanoylamino]-2-hydroxy-propyl}-cyclohexylmethyl-phosphinic acid (0.399 g, 0.893 mmol). NMR and MS spectra were substantially similar to the product obtained in Method A.

Examples 13A and 13B

Example 13A

{(R)-3-[(S)-2-((S)-2-Amino-3-methyl-butyrylamino)-3-methyl-pentanoylamino]-2-hydroxy-propyl}-cyclohexylmethyl-phosphinic acid, and Example 13B {(R)-3-[(R)-2-((S)-2-Amino-3-methyl-butyrylamino)-3-methyl-pentanoylamino]-2-hydroxy-propyl}-cyclohexylmethyl-phosphinic acid Example 13A

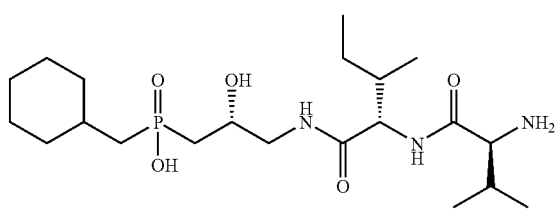

Example 13B

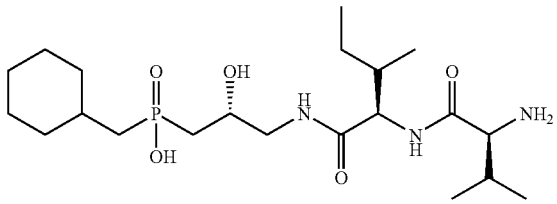

The title compounds were prepared as a mixture of diastereomers from ((R)-3-amino-2-hydroxy-propyl)-cyclohexylmethyl-phosphinic acid benzyl ester hydrochloride, substantially following the procedures as set forth in Method A, Example 12, and using N-Cbz-L-valine-L-isoleucine-OH. The mixture was purified by RP-HPLC using 10-40% CH$_3$CN/(HCl/H$_2$O, pH=3.5) over 18 min at 70 mL/min. The first fraction was lyophilized to give {(R)-3-[(S)-2-((S)-2-amino-3-methyl-butyrylamino)-3-methyl-pentanoylamino]-2-hydroxy-propyl}-cyclohexylmethyl-phosphinic acid. $^1$H NMR (CD$_3$OD, 300 MHz): δ 4.23 (d, 1H), 4.12-3.95 (m, 1H), 3.75 (d, 1H), 3.38-3.20 (m, 2H), 2.31-2.13 (m, 1H), 1.93 (br d, 2H), 1.91-1.58 (dd, 8H), 1.40-1.15 (m, 4H), 1.10-0.85 (m, 14H). $^{31}$P NMR (CD$_3$OD, 300 MHz): δ 42.96. LCMS m/z: [M+H]$^+$=448.2. The second fraction gave {(R)-3-[(R)-2-((S)-2-amino-3-methyl-butyrylamino)-3-methyl-pentanoylamino]-2-hydroxy-propyl}-cyclohexylmethyl-phosphinic acid. $^1$H NMR (CD$_3$OD, 300 MHz): δ 4.40 (d, 1H), 4.06-3.92 (m, 1H), 3.75 (d, 1H), 3.57 (dd, 1H), 3.13 (dd, 1H), 2.22-2.05 (m, 2H), 1.99-1.85 (m, 2H), 1.84-1.58 (m, 6H), 1.57-1.43 (m, 2H), 1.40-1.13 (m, 5H), 1.10-0.98 (m, 8H), 0.97-0.88 (m, 6H). $^{31}$P NMR (CD$_3$OD, 300 MHz): δ 42.28. LCMS m/z: [M+H]$^+$=448.3.

Example 14

{(R)-3-[2-((S)-2-Amino-3-methyl-butyrylamino)-acetylamino]-2-hydroxy-propyl}-cyclohexylmethyl-phosphinic acid hydrate

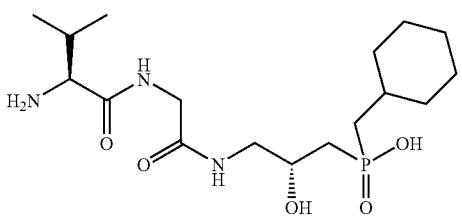

The title compound was prepared as a single diastereoisomer from ((R)-3-amino-2-hydroxy-propyl)-cyclohexylmethyl-phosphinic acid benzyl ester hydrochloride, substantially following the procedures as set forth in Method A, Example 12, and using N-cbz-L-valine-L-glycine-OH. The crude material was purified by RP-HPLC using 10-40% CH$_3$CN/(HCl/H$_2$O, pH=3.5) over 18 min at 70 mL/min. The pure fractions were combined and concentrated to dryness to give {(R)-3-[2-((S)-2-amino-3-methyl-butyrylamino)-acetylamino]-2-hydroxy-propyl}-cyclohexylmethyl-phosphinic acid hydrate as white powder crystals. $^1$H NMR (CD$_3$OD, 300 MHz): δ 4.14 (d, 1H), 4.08-3.94 (m, 1H), 3.72-3.60 (m, 2H), 3.50 (dd, 1H), 3.20 (dd, 1H), 2.24-2.10 (m, 1H), 2.02-

1.60 (m, 8H), 1.52 (dd, 2H), 1.42-0.96 (m, 11H). $^{31}$P NMR (CD$_3$OD, 300 MHz): δ 41.8. LCMS m/z: [M+H]$^+$=392.2.

Examples 15A and 15B

Example 15A

{(R)-3-[(S)-2-((S)-2-Amino-3-methyl-butyrylamino)-propionylamino]-2-hydroxy-propyl}-cyclohexylmethyl-phosphinic acid hydrate, and

Example 15B

{(R)-3-[(R)-2-((S)-2-Amino-3-methyl-butyrylamino)-propionylamino]-2-hydroxy-propyl}-cyclohexylmethyl-phosphinic acid hydrate

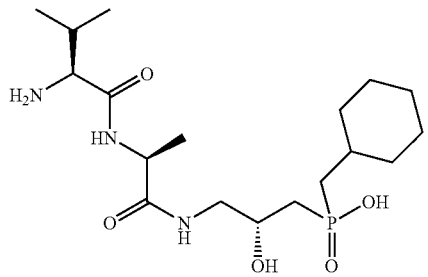

Example 15A

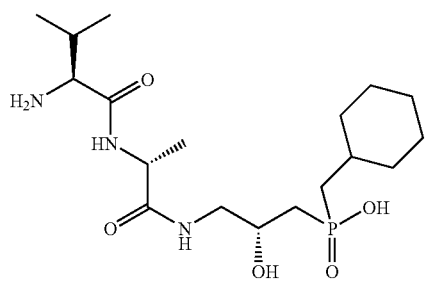

Example 15B

The title compounds were prepared as a mixture of diastereomers from ((R)-3-amino-2-hydroxy-propyl)-cyclohexylmethyl-phosphinic acid benzyl ester hydrochloride, substantially following the procedures as set forth in Method A, Example 12, and using N-cbz-L-valine-L-alanine-OH. The mixture was purified by RP-HPLC using 10-40% CH$_3$CN/(HCl/H$_2$O, pH=3.5) over 18 min at 70 mL/min. The first fraction was lyophilized to give {(R)-3-[(S)-2-((S)-2-amino-3-methyl-butyrylamino)-propionylamino]-2-hydroxy-propyl}-cyclohexylmethyl-phosphinic acid hydrate as a white powder. $^1$H NMR (CD$_3$OD, 300 MHz): δ 4.34 (q, 1H), 4.08-3.96 (m, 1H), 3.66 (d, 1H), 3.32-3.26 (m, 2H), 2.29-2.14 (m, 1H), 1.97-1.85 (m, 2H), 1.82-1.51 (m, 8H), 1.40 (d, 3H), 1.35-0.95 (m, 11H). $^{31}$P NMR (CD$_3$OD, 300 MHz): δ 41.8. LCMS m/z: [M+H]$^+$=406.3. The second fraction was lyophilized to give {(R)-3-[(R)-2-((S)-2-amino-3-methyl-butyrylamino)-propionylamino]-2-hydroxy-propyl}-cyclohexylmethyl-phosphinic acid hydrate as a white powder. $^1$H NMR (CD$_3$OD, 300 MHz): δ 4.36 (q, 1H), 4.07-3.94 (m, 1H), 3.62 (d, 1H), 3.46 (dd, 1H), 3.19 (dd, 1H), 2.24-2.07 (m, 1H), 1.99-1.61 (m, 8H), 1.61-1.51 (m, 2H), 1.40 (d, 3H), 1.37-0.97 (m, 11H). $^{31}$P NMR (CD$_3$OD, 300 MHz): δ 44.2. LCMS m/z: [M+H]$^+$=406.3.

Examples 16A and 16B

Example 16A

{(R)-3-[(S)-2-((S)-2-Amino-3-phenyl-propionylamino)-3-methyl-butyrylamino]-2-hydroxy-propyl}-cyclohexylmethyl-phosphinic acid, and

Example 16B

{(R)-3-[(R)-2-((S)-2-Amino-3-phenyl-propionylamino)-3-methyl-butyrylamino]-2-hydroxy-propyl}-cyclohexylmethyl-phosphinic acid

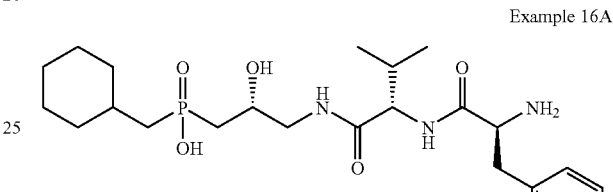

Example 16A

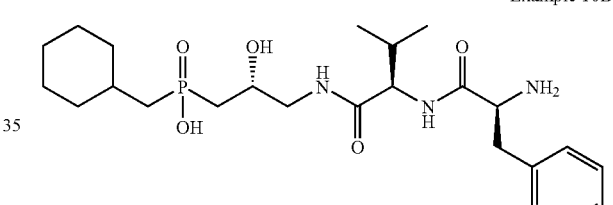

Example 16B

Step 1: {(R)-3-[(S)-2-((S)-2-Benzyloxycarbonylamino-3-phenyl-propionylamino)-3-methyl-butyrylamino]-2-hydroxy-propyl}-cyclohexylmethyl-phosphinic acid benzyl ester and {(R)-3-[(R)-2-((S)-2-benzyloxycarbonylamino-3-phenyl-propionylamino)-3-methyl-butyrylamino]-2-hydroxy-propyl}-cyclohexylmethyl-phosphinic acid benzyl ester: To a solution of N-Z-Phe-Val-OH (1.0 g, 2.5 mmol) dissolved in CH$_2$Cl$_2$ (80 mL) under nitrogen was added hydroxybenzotriazole (0.346 g, 2.56 mmol) and PS-Carbodiimide (1.3 g, 3.0 mmol). After stirring for 10 min, triethylamine (1.4 mL, 10 mmol) and ((R)-3-amino-2-hydroxy-propyl)-cyclohexylmethyl-phosphinic acid benzyl ester hydrochloride (1.36 g, 3.75 mmol) were added. The reaction was stirred for 2 h, then filtered and concentrated in vacuo. The residue was purified by flash chromatography using 0-4% MeOH/CH$_2$Cl$_2$ as the eluent on a 35 g RediSep disposable column to give the title compound (0.806 g, 1.14 mmol) as a glassy solid. $^{31}$P NMR (CD$_3$OD, 300 MHz): δ 59.09, 59.09, 58.38, 58.38. LCMS m/z: [M+H]$^+$=707.

Step 2: {(R)-3-[(S)-2-((S)-2-Amino-3-phenyl-propionylamino)-3-methyl-butyrylamino]-2-hydroxy-propyl}-cyclohexylmethyl-phosphinic acid and {(R)-3-[(R)-2-((S)-2-amino-3-phenyl-propionylamino)-3-methyl-butyrylamino]-2-hydroxy-propyl}-cyclohexylmethyl-phosphinic acid: The diastereomeric mixture from Step 1, Example 16 (0.8 g, 1.13 mmol) was dissolved in ethanol (35 mL) and was hydrogenated via a hydrogen Paar shaker for 2 h at 50 psi with 10%

Pd/C (0.3 g) as a catalyst. The reaction was filtered through celite and concentrated in vacuo to give an oil. The residue was purified by RP-HPLC eluting in a gradient of 10% $CH_3CN/H_2O$ (adjusted with HCl to pH=3.5) to 100% $CH_3CN$. The appropriate fractions were combined and lyophilized to give the title compounds. The first fraction was isolated as a white solid and characterized to be {(R)-3-[(S)-2-((S)-2-amino-3-phenyl-propionylamino)-3-methyl-butyrylamino]-2-hydroxy-propyl}-cyclohexylmethyl-phosphinic acid (0.31 g, 0.64 mmol). $^1$H NMR($CD_3OD$, 300 MHz): δ 7.35-7.25 (m, 5H), 4.21 (m, 2H), 4.04 (q, 2H), 3.33 (m, 1H), 3.05 (dd, 1H), 2.1 (m, 1H), 1.90 (m, 2H), 1.74-1.65 (m, 6H), 1.5-1.45 (m, 2H), 1.30-1.20 (m, 3H), 1.01-0.90 (m, 8H). $^{31}$P NMR ($CD_3OD$, 300 MHz): δ 42.32. LCMS m/z: $[M+H]^+$=482. The second fraction was also isolated as a white solid and characterized to be {(R)-3-[(R)-2-((S)-2-amino-3-phenyl-propionylamino)-3-methyl-butyrylamino]-2-hydroxy-propyl}-cyclohexylmethyl-phosphinic acid (0.03 g, 0.06 mmol). $^1$H-NMR($CD_3OD$, 300 MHz): δ 7.35-7.24 (m, 5H), 4.21 (m, 2H), 4.04 (m, 2H), 3.50 (m, 1H), 3.05 (m, 1H), 2.10 (m, 1H), 1.90 (m, 2H), 1.74-1.65 (m, 6H), 1.50-1.45 (m, 2H), 1.30-1.20 (m, 3H), 1.15 (m, 2H), 0.70-0.60 (dd, 6H). $^{31}$P NMR ($CD_3OD$, 300 MHz): δ 43.76. LCMS m/z: $[M+H]^+$=482.

Examples 17A and 17B

Example 17A

{(R)-3-[(S)-2-((S)-2-Amino-3-methyl-butyrylamino)-3-methyl-butyrylamino]-2-hydroxy-propyl}-cyclohexylmethyl-phosphinic acid, and Example 17B {(R)-3-[(R)-2-((S)-2-Amino-3-methyl-butyrylamino)-3-methyl-butyrylamino]-2-hydroxy-propyl}-cyclohexylmethyl-phosphinic acid Example 17A

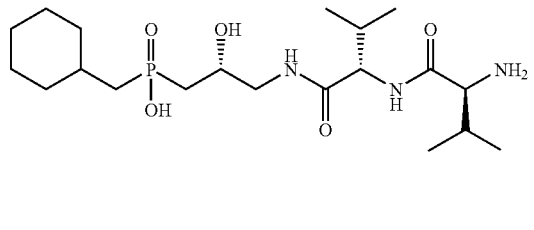

Example 17B

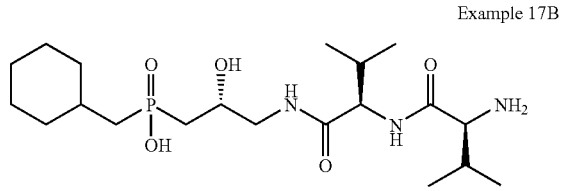

Step 1: {(R)-3-[(S)-2-((S)-2-Benzyloxycarbonylamino-3-methyl-butyrylamino)-3-methyl-butyrylamino]-2-hydroxy-propyl}-cyclohexylmethyl-phosphinic acid benzyl ester and {(R)-3-[(R)-2-((S)-2-benzyloxycarbonylamino-3-methyl-butyrylamino)-3-methyl-butyrylamino]-2-hydroxy-propyl}-cyclohexylmethyl-phosphinic acid benzyl ester: The title compounds were prepared substantially in a similar manner as Step 1 of Example 16 using N-Z-Val-Val-OH. Purification by flash chromatography using 0-4% $MeOH/CH_2Cl_2$ as the eluent on a 35 g RediSep disposable column gave the diastereomeric mixture. $^1$H NMR ($CD_3OD$, 300 MHz): δ 7.33 (m, 10H), 5.02 (m, 4H), 4.21-3.88 (m, 3H), 3.32 (m, 2H), 2.20 (m, 1H), 2.08 (m, 1H), 1.90 (m, 2H), 1.74-1.66 (m, 6H), 1.5-1.47 (m, 2H), 1.33 (m, 2H), 1.19 (m, 1H), 1.03-0.99 (m, 14H). $^{31}$P NMR ($CD_3OD$, 300 MHz): δ 60.63, 60.57, 59.87, 59.84. LCMS m/z: $[M+H]^+$=659.

Step 2: {(R)-3-[(S)-2-((S)-2-Amino-3-methyl-butyrylamino)-3-methyl-butyrylamino]-2-hydroxy-propyl}-cyclohexylmethyl-phosphinic acid and {(R)-3-[(R)-2-((S)-2-amino-3-methyl-butyrylamino)-3-methyl-butyrylamino]-2-hydroxy-propyl}-cyclohexylmethyl-phosphinic acid: The title compounds were prepared substantially in a similar manner as Step 2 of Example 16. Purification by RP-HPLC eluting in a gradient of 10% $CH_3CN/H_2O$ (adjusted with HCl pH=3.5) to 100% $CH_3CN$ yielded the desired compounds. The first fraction gave {(R)-3-[(S)-2-((S)-2-amino-3-methyl-butyrylamino)-3-methyl-butyrylamino]-2-hydroxy-propyl}-cyclohexylmethyl-phosphinic acid. $^1$H NMR($CD_3OD$, 300 MHz): δ 4.21 (d, 1H), 4.04 (q, 1H), 3.79 (d, 1H), 3.33 (dd, 1H), 3.25 (m, 1H), 2.20 (m, 1H), 2.08 (m, 1H), 1.90 (m, 2H), 1.74-1.66 (m, 6H), 1.5-1.47 (m, 2H), 1.33 (m, 2H), 1.19 (m, 1H), 1.03 (dd, 6H), 1.01-0.99 (m, 8H). $^{31}$P NMR ($CD_3OD$, 300 MHz): δ 40.75. LCMS m/z: $[M+H]^+$=435.

The second fraction yielded {(R)-3-[(R)-2-((S)-2-amino-3-methyl-butyrylamino)-3-methyl-butyrylamino]-2-hydroxy-propyl}-cyclohexylmethyl-phosphinic acid. $^1$H NMR ($CD_3OD$, 300 MHz): δ 4.19 (d, 1H), 4.00 (q, 1H), 3.73 (d, 1H), 3.53 (dd, 1H), 3.10 (m, 1H), 2.28 (m, 1H), 2.15 (m, 1H), 1.92 (m, 2H), 1.77-1.64 (m, 6H), 1.50 (m, 2H), 1.30 (m, 2H), 1.18 (m, 1H), 1.07-1.02 (m, 8H), 0.96 (dd, 6H). $^{31}$P NMR ($CD_3OD$, 300 MHz): δ 40.78. LCMS m/z: $[M+H]^+$=435.

Example 18

{(R)-3-[(S)-2-((S)-2-Amino-4-methyl-pentanoylamino)-3-methyl-butyrylamino]-2-hydroxy-propyl}-cyclohexylmethyl-phosphinic acid

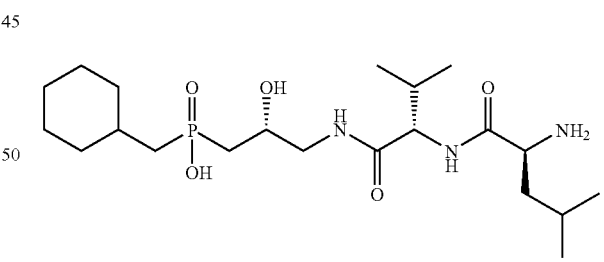

Step 1: {(R)-3-[(S)-2-((S)-2-Benzyloxycarbonylamino-4-methyl-pentanoylamino)-3-methyl-butyrylamino]-2-hydroxy-propyl}-cyclohexylmethyl-phosphinic acid benzyl ester: The title compound was prepared substantially in a similar manner as Step 1 of Example 10 using N-Z-Leu-OH and [(R)-3-((S)-2-amino-3-methyl-butyrylamino)-2-hydroxy-propyl]-cyclohexylmethyl-phosphinic acid benzyl ester hydrochloride as the starting materials. The title compound was purified by $SiO_2$ chromatography using 0-4% $MeOH/CH_2Cl_2$ as the eluent. $^1$H NMR ($CD_3OD$, 300 MHz): δ 7.34 (m, 10H), 5.50 (m, 4H), 4.19 (m, 2H), 4.01-3.94 (m, 1H), 3.30 (m, 2H), 2.15 (m, 1H), 1.92 (m, 2H), 1.77-1.64 (m, 8H), 1.50 (m, 2H), 1.40-1.12 (m, 4H), 1.11-0.97 (m, 14H). $^{31}$P NMR (CD$_3$OD, 300 MHz): δ 60.56, 59.87. LCMS m/z: [M+H]$^+$=672.

Step 2: {(R)-3-[(S)-2-((S)-2-Amino-4-methyl-pentanoylamino)-3-methyl-butyrylamino]-2-hydroxy-propyl}-cyclohexylmethyl-phosphinic acid: The title compound was prepared substantially in a similar manner as Step 2 of Example 10 using {(R)-3-[(S)-2-((S)-2-benzyloxycarbonylamino-4-methyl-pentanoylamino)-3-methyl-butyrylamino]-2-hydroxy-propyl}-cyclohexylmethyl-phosphinic acid benzyl ester as the starting material. $^1$H NMR (CD$_3$OD, 300 MHz): δ 4.19 (d, 1H), 4.01-3.94 (m, 2H), 3.30 (m, 2H), 2.15 (m, 1H), 1.92 (m, 2H), 1.77-1.64 (m, 8H), 1.50 (m, 2H), 1.40-1.12 (m, 4H), 1.11-0.97 (m, 14H). $^{31}$P NMR (CD$_3$OD, 300 MHz): δ 41.83. LCMS m/z: [M+H]$^+$=447.

Example 19

Cyclohexylmethyl-((R)-2-hydroxy-3-{(S)-3-methyl-2-[((S)-pyrrolidine-2-carbonyl)-amino]-butyrylamino}-propyl)-phosphinic acid

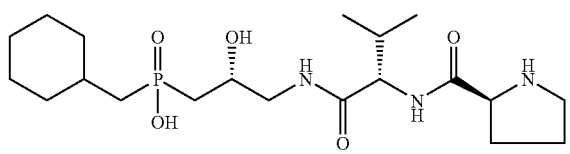

Step 1: (S)-2-{(S)-1-[(R)-3-(Benzyloxy-cyclohexylmethyl-phosphinoyl)-2-hydroxy-propylcarbamoyl]-2-methyl-propylcarbamoyl}-pyrrolidine-1-carboxylic acid benzyl ester: The title compound was prepared substantially in a similar manner as Step 1 of Example 10 using N-Z-pro-OH and [(R)-3-((S)-2-amino-3-methyl-butyrylamino)-2-hydroxy-propyl]-cyclohexylmethyl-phosphinic acid benzyl ester hydrochloride as the starting materials. The title compound was purified by SiO$_2$ chromatography using 0-4% MeOH/CH$_2$Cl$_2$ as the eluent. $^1$H NMR (CD$_3$OD, 300 MHz): δ 7.35 (m, 10H), 5.05 (m, 4H), 4.35 (m, 1H), 4.09 (m, 1H), 4.02 (m, 1H), 3.56-3.44 (m, 2H), 3.25 (m, 2H), 2.21 (m, 1H), 1.96-1.63 (m, 12H), 1.27-0.81 (m, 14H). $^{31}$P NMR (CD$_3$OD, 300 MHz): δ 60.53, 59.84. LCMS m/z: [M+H]$^+$=656.

Step 2: Cyclohexylmethyl-((R)-2-hydroxy-3-{(S)-3-methyl-2-[((S)-pyrrolidine-2-carbonyl)-amino]-butyrylamino}-propyl)-phosphinic acid: The title compound was prepared substantially in a similar manner as Step 2 of Example 10 using (S)-2-{(S)-1-[(R)-3-(benzyloxy-cyclohexylmethyl-phosphinoyl)-2-hydroxy-propylcarbamoyl]-2-methyl-propylcarbamoyl}-pyrrolidine-1-carboxylic acid benzyl ester as the starting material. $^1$H NMR (CD$_3$OD, 300 MHz): δ 4.39 (q, 1H), 4.22 (d, 1H), 4.02 (m, 1H), 3.45-3.34 (m, 3H), 3.25 (m, 1H), 2.40 (m, 1H), 2.09 (m, 3H), 1.90 (m, 2H), 1.74-1.66 (m, 6H), 1.5-1.45 (m, 2H), 1.32-1.19 (m, 3H), 1.10-0.95 (m, 9H). $^{31}$P NMR (CD$_3$OD, 300 MHz): δ 41.83. LCMS m/z: [M+H]$^+$=432.

Example 20

{(R)-3-[(S)-2-((S)-2-Amino-3-methyl-pentanoylamino)-3-methyl-butyrylamino]-2-hydroxy-propyl}-cyclohexylmethyl-phosphinic acid

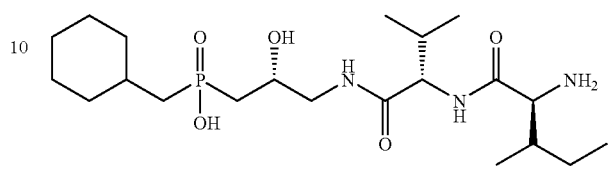

Step 1: {(R)-3-[(S)-2-((S)-2-Benzyloxycarbonylamino-3-methyl-pentanoylamino)-3-methyl-butyrylamino]-2-hydroxy-propyl}-cyclohexylmethyl-phosphinic acid benzyl ester: The title compound was prepared substantially in a similar manner as Step 1, Example 10 using N-Z-Ile-OH and [(R)-3-((S)-2-amino-3-methyl-butyrylamino)-2-hydroxy-propyl]-cyclohexylmethyl-phosphinic acid benzyl ester hydrochloride as the starting materials. The title compound was purified by SiO$_2$ chromatography using 0-4% MeOH/CH$_2$Cl$_2$ as the eluent. $^1$H NMR (CD$_3$OD, 300 MHz): δ 7.3 (m, 10H), 5.2-4.95 (m, 4H), 4.17 (d, 1H), 4.12 (m, 1H), 3.95 (d, 1H), 3.20 (m, 2H), 2.12-2.01 (m, 1H), 1.90-1.76 (m, 3H), 1.70-1.61 (m, 6H), 1.55-1.47 (m, 3H), 1.36-1.14 (m, 4H), 1.11-0.95 (m, 14H). $^{31}$P NMR (CD$_3$OD, 300 MHz): δ 59.06, 58.33. LCMS m/z: [M+H]$^+$=672.

Step 2: {(R)-3-[(S)-2-((S)-2-Amino-3-methyl-pentanoylamino)-3-methyl-butyrylamino]-2-hydroxy-propyl}-cyclohexylmethyl-phosphinic acid: The title compound was prepared substantially in a similar manner as Step 2, Example 10 using as the starting material {(R)-3-[(S)-2-((S)-2-benzyloxycarbonylamino-3-methyl-pentanoylamino)-3-methyl-butyrylamino]-2-hydroxy-propyl}-cyclohexylmethyl-phosphinic acid benzyl ester. $^1$H NMR (CD$_3$OD, 300 MHz): δ 4.17 (d, 1H), 4.02 (q, 1H), 3.78 (d, 1H), 3.30 (dd, 1H), 3.27 (m, 1H), 2.12-2.01 (m, 1H), 1.90-1.76 (m, 3H), 1.70-1.61 (m, 6H), 1.55-1.47 (m, 3H), 1.36-1.14 (m, 4H), 1.11-0.95 (m, 14H). $^{31}$P NMR (CD$_3$OD, 300 MHz): δ 42.1. LCMS m/z: [M+H]$^+$=448.

Example 21

(S)-2-{(R)-2-Amino-4-[(R)-3-(cyclohexylmethyl-hydroxy-phosphinoyl)-2-hydroxy-propylcarbamoyl]-butyrylamino}-propionic acid

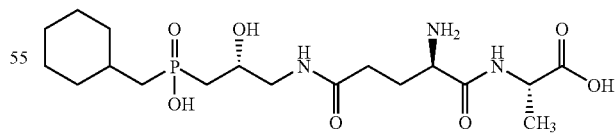

Step 1: (S)-2-{(R)-4-[(R)-3-(Benzyloxy-cyclohexylmethyl-phosphinoyl)-2-hydroxy-propylcarbamoyl]-2-tert-butoxycarbonylamino-butyrylamino}-propionic acid tert-butyl ester: The title compound was prepared substantially in a similar manner as Step 1, Example 11 using (R)-4-tert-butoxycarbonylamino-4-((S)-1-tert-butoxycarbonyl-ethylcarbamoyl)-butyric acid (prepared in accordance with the procedures set forth in *Eur. J. Pharm. Sci.*, 14, 2001, 13-19). $^1$H NMR (CDCl₃, 300 MHz): δ 7.35 (m, 5H), 6.69 (br d, 1H), 5.55 (br s, 1H), 5.03 (m, 2H), 4.46 (m, 1H), 4.40 (m, 1H), 4.18 (m, 1H), 3.40 (m, 2H), 2.30 (m, 2H), 2.10-1.60 (m, 10H), 1.53 (s, 9H), 1.43 (s, 9H), 1.36 (d, J=7.2 Hz, 3H), 1.28-1.10 (m, 3H), 1.09-1.00 (m, 4H). LCMS m/z: [M+H]⁺=682.38.

Step 2: (S)-2-{(R)-2-tert-Butoxycarbonylamino-4-[(R)-3-(cyclohexylmethyl-hydroxy-phosphinoyl)-2-hydroxy-propylcarbamoyl]-butyrylamino}-propionic acid tert-butyl ester: The title compound was prepared substantially in a similar manner as Step 5, Example 1, Method A using (S)-2-{(R)-4-[(R)-3-(benzyloxy-cyclohexylmethyl-phosphinoyl)-2-hydroxy-propylcarbamoyl]-2-tert-butoxycarbonylamino-butyrylamino}-propionic acid tert-butyl ester as the starting material. The compound thus formed was used in the next step without further purification. LCMS m/z: [M+H]⁺=592.30.

Step 3: (S)-2-{(R)-2-Amino-4-[(R)-3-(cyclohexylmethyl-hydroxy-phosphinoyl)-2-hydroxy-propylcarbamoyl]-butyrylamino}-propionic acid: 4N HCl in dioxane (5 mL) was added to (S)-2-{(R)-2-tert-butoxycarbonylamino-4-[(R)-3-(cyclohexylmethyl-hydroxy-phosphinoyl)-2-hydroxy-propylcarbamoyl]-butyrylamino}-propionic acid tert-butyl ester (0.351 g, 0.592 mmol) in water (1 mL). The resulting colorless solution was stirred under N₂ at rt overnight. The reaction mixture was concentrated in vacuo and the residue was purified by RP-HPLC eluting in a gradient of 10% CH₃CN/H₂O (adjusted with HCl pH=3.5) to 100% CH₃CN over 20 min at 45 mL/min. The appropriate fractions were combined and lyophilized to give the title compound (0.096 g, 0.220 mmol) as a white solid. ¹H NMR (CD₃OD, 300 MHz): δ 4.38 (q, J=7.2 Hz, 1H), 4.04 (m, 1H), 3.90 (t, J=6.3 Hz, 1H), 3.35 (dd, J=5.7, 13.2 Hz, 1H), 3.21 (dd, J=5.7, 13.5 Hz, 1H), 2.41 (m, 2H), 2.11 (m, 2H), 1.92 (br d, 2H), 1.77-1.65 (m, 6H), 1.52 (dd, J=6.3, 13.5 Hz, 2H), 1.43 (d, J=7.2 Hz, 3H), 1.37-1.15 (m, 3H), 1.08-1.00 (m, 2H). ³¹P NMR (CD₃OD, 300 MHz): δ 42.95. LCMS m/z: [M+H]⁺=436.25

Example 22

{(R)-3-[(S)-2-((S)-2-Amino-3-methyl-butyrylamino)-3-phenyl-propionylamino]-2-hydroxy-propyl}-cyclohexylmethyl-phosphinic acid

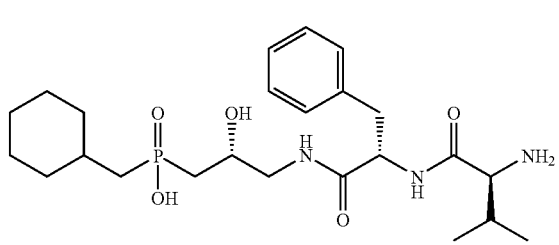

The title compound was prepared substantially following the procedures as set forth in Method B, Example 12, and employing ((R)-3-amino-2-hydroxy-propyl)-cyclohexylmethyl-phosphinic acid benzyl ester hydrochloride and N-cbz-L-valine-L-phenylalanine-OH as the starting materials, which yielded the title compound as a white powder. ¹H NMR (CD₃OD, 300 MHz): δ 7.33-7.15 (m, 5H), 4.60-4.53 (m, 1H), 4.08-3.93 (m, 1H), 3.61 (d, 1H), 3.38-3.28 (m, 2H), 3.27-3.18 (m, 1H), 3.10-3.02 (m, 1H), 2.18-2.03 (m, 1H), 1.93 (br d., 2H), 1.80-1.58 (m, 6H), 1.46 (dd, 2H), 1.41-1.13 (m, 3H), 1.10-0.90 (m, 8H). ³¹P NMR (CD₃OD, 300 MHz): δ 40.45. LCMS m/z: [M+H]⁺=482.3.

Example 23

{(R)-3-[(S)-2-((S)-2-Amino-3-methyl-butyrylamino)-3-(4-hydroxy-phenyl)-propionylamino]-2-hydroxy-propyl}-cyclohexylmethyl-phosphinic acid

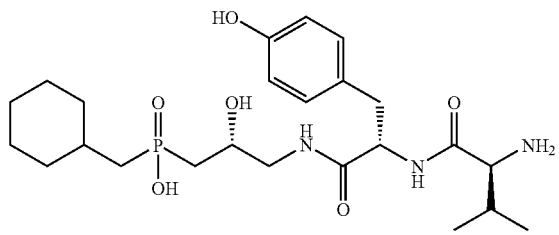

The title compound was prepared substantially following the procedures as set forth in Method B, Example 12, and employing ((R)-3-amino-2-hydroxy-propyl)-cyclohexylmethyl-phosphinic acid benzyl ester hydrochloride and N-cbz-L-valine-L-tyrosine-OH as the starting materials, which yielded the title compound as an off white powder. ¹H NMR (CD₃OD, 300 MHz): δ 7.10 (d, 2H), 6.73 (d, 2H), 4.58-4.42 (m, 1H), 4.10-3.91 (m, 1H), 3.63 (d, 1H), 3.38-3.20 (m, 2H), 3.15-3.02 (m, 1H), 3.00-2.85 (m, 1H), 2.20-2.05 (m, 1H), 1.93 (br d., 2H), 1.82-1.58 (m, 6H), 1.48 (dd, 2H), 1.40-1.10 (m, 3H), 1.08-0.93 (m, 8H). ³¹P NMR (CD₃OD, 300 MHz): δ 40.47. LCMS m/z: [M+H]⁺=498.3.

Example 24

((R)-3-{[(S)-1-((S)-2-Amino-3-methyl-butyryl)-pyrrolidine-2-carbonyl]-amino}-2-hydroxy-propyl)-cyclohexylmethyl-phosphinic acid

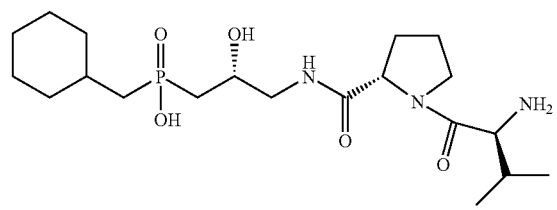

The title compound was prepared substantially following the procedures as set forth in Method B, Example 12, and employing ((R)-3-amino-2-hydroxy-propyl)-cyclohexylmethyl-phosphinic acid benzyl ester hydrochloride and N-cbz-L-valine-L-proline-OH as the starting materials, which yielded the title compound as a white powder. ¹H NMR (CD₃OD, 300 MHz): δ 4.55-4.41 (m, 1H), 4.13-3.98 (m, 2H), 3.80-3.40 (m, 3H), 3.30-3.18 (m, 1H), 2.40-2.08 (m, 3H), 2.03-1.85 (m, 4H), 1.83-1.58 (m, 6H), 1.55-1.43 (m, 2H), 1.41-1.18 (m, 3H), 1.13 (d, 2H), 1.11-0.94 (m, 6H). ³¹P NMR (CD₃OD, 300 MHz): δ 40.51, 39.63. LCMS m/z: [M+H]⁺=432.2.

Example 25

((R)-3-{(S)-2-[(S)-2-Amino-3-(1H-indol-3-yl)-propionylamino]-3-methyl-butyrylamino}-2-y-propyl)-cyclohexylmethyl-phosphinic acid

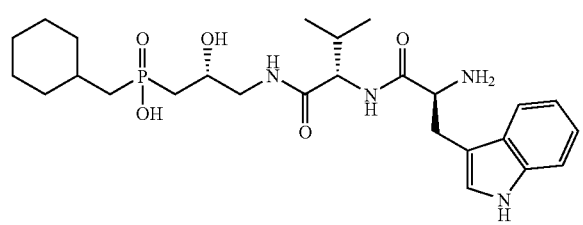

The title compound was prepared substantially following the procedures as set forth in Method B, Example 12, and employing ((R)-3-amino-2-hydroxy-propyl)-cyclohexylmethyl-phosphinic acid benzyl ester hydrochloride and N-Cbz-Trp-Val-OH as the staring materials, which yielded the title compound as a white powder. $^1$H NMR (CD$_3$OD, 300 MHz): δ 7.65-7.62 (d, 1H), 7.38-7.35 (d, 1H), 7.17-7.01 (m, 3H), 4.26-4.20 (m, 1H), 4.17-4.14 (d, 1H), 4.05 (m, 1H), 3.46-3.20 (m, 4H), 2.00 (m, 1H), 1.9-1.88 (m, 2H), 1.77-1.54 (m, 8H), 1.34-1.16 (m, 3H), 1.05-0.94 (m, 8H). $^{31}$P NMR (CD$_3$OD, 300 MHz): δ 42.89. LCMS m/z: [M+H]$^+$=521.

Example 26

((R)-3-{(S)-2-[(S)-2-Amino-3-(4-hydroxy-phenyl)-propionylamino]-3-methyl-butyrylamino}-2-hydroxy-propyl)-cyclohexylmethyl-phosphinic acid

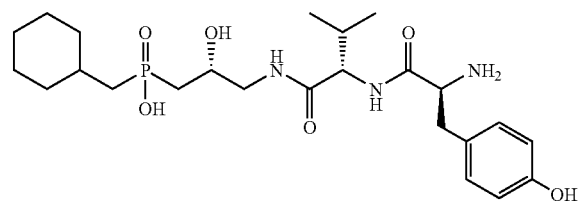

The title compound was prepared substantially following the procedures as set forth in Method B, Example 12, and employing ((R)-3-amino-2-hydroxy-propyl)-cyclohexylmethyl-phosphinic acid benzyl ester hydrochloride and N-Cbz-Tyr-Val-OH as the starting materials, which yielded the title compound as a white powder. $^1$H NMR (CD$_3$OD, 300 MHz): δ 7.06 (d, 2H), 6.75 (d, 2H), 4.15-4.06 (m, 2H), 3.18-3.10 (m, 2H), 3.0-2.9 (m, 1H), 2.09-2.02 (m, 1H), 1.92-1.88 (m, 2H), 1.86-1.61 (m, 6H), 1.56-1.50 (m, 3H), 1.30-1.17 (m, 4H), 1.06-0.95 (m, 8H). $^{31}$P NMR (CD$_3$OD, 300 MHz): δ 41.72. LCMS m/z: [M+H]$^+$=498.

Example 27

[(R)-3-((R)-2-Amino-propionylamino)-2-hydroxy-propyl]-cyclohexylmethyl-phosphinic acid

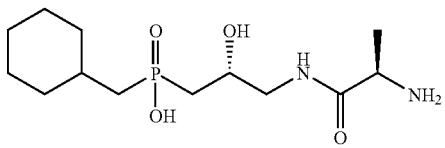

The title compound was prepared substantially following the procedures as set forth in Step 4, Example 1, Method B and employing ((R)-3-amino-2-hydroxy-propyl)-cyclohexylmethyl-phosphinic acid benzyl ester hydrochloride and N-Cbz-D-alanine as the starting materials. Subsequent hydrogenation of the resulting product in accordance with the procedures of Step 5, Example 1, Method B, and RP-HPLC purification yielded the title compound. $^1$H NMR (CD$_3$OD, 300 MHz): δ 4.04 (m, 1H), 3.89 (q, J=6.9 Hz, 1H), 3.39 (dd, J=5.7, 13.5, 1H), 3.23 (dd, J=5.4, 13.5 Hz, 1H), 1.85 (m, 2H), 1.77-1.62 (m, 6H), 1.57-1.53 (m, 2H), 1.48 (d, J=6.9 Hz, 3H), 1.37-1.15 (m, 3H), 1.08-0.97 (m, 2H). $^{31}$P NMR (CD$_3$OD, 300 MHz): δ 43.74. LCMS m/z: [M+H]$^+$=307.2.

Example 28

{(R)-3-[(S)-2-((S)-2-Amino-3-methyl-butyrylamino)-3-(1H-indol-3-yl)-propionylamino]-2-hydroxy-propyl}-cyclohexylmethyl-phosphinic acid

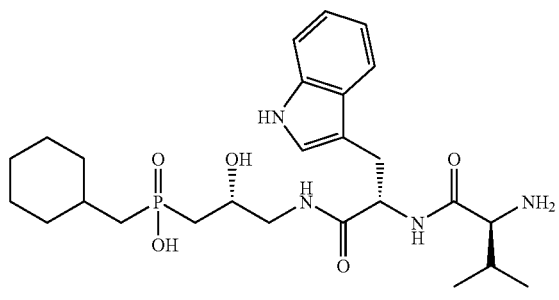

The title compound was prepared substantially following the procedures as set forth in Method B, Example 12, and employing ((R)-3-amino-2-hydroxy-propyl)-cyclohexylmethyl-phosphinic acid benzyl ester hydrochloride and N-cbz-L-valine-L-tryptophan-OH as the starting materials, which yielded the title compound as a white powder. $^1$H NMR (CD$_3$OD, 300 MHz): δ 7.61 (d, 1H), 7.33 (d, 1H), 7.18-6.93 (m, 3H), 4.72 (t, 1H), 4.06-3.90 (m, 1H), 3.69 (d, 1H), 3.39-3.10 (m, 4H), 2.23-2.07 (m, 1H), 1.93 (br.d., 2H), 1.82-1.52 (m, 6H), 1.51-1.38 (m, 2H), 1.37-1.10 (m, 3H), 1.08-0.90 (m, 8H). $^{31}$P NMR (CD$_3$OD, 300 MHz): δ 40.87. LCMS m/z: [M+H]$^+$=521.29.

Example 29

(S)-4-Amino-4-[(R)-3-(cyclohexylmethyl-hydroxy-phosphinoyl)-2-hydroxy-propylcarbamoyl]-butyric acid

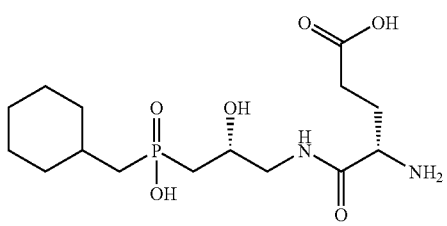

The title compound was prepared substantially following the procedures as set forth in Step 4, Example 1, Method A, and employing ((R)-3-Amino-2-hydroxy-propyl)-cyclohexylmethyl-phosphinic acid benzyl ester hydrochloride and N-Cbz-L-glutamic acid(OBzl)-OH as the starting materials. Subsequent hydrogenation of the resulting product in accordance with the procedures of Step 5, Example 1, Method B, and RP-HPLC purification yielded the title compound. $^1$H NMR (CD$_3$OD, 300 MHz): δ 4.18-4.01 (m, 1H), 3.93 (t, 1H), 3.44-3.36 (m, 1H), 3.34-3.24 (m, 1H), 2.50 (t, 2H), 2.21-2.08 (m, 2H), 1.93 (br.d., 2H), 1.85-1.60 (m, 6H), 1.59-1.45 (m, 2H), 1.42-1.15 (m, 3H), 1.14-0.95 (m, 2H). $^{31}$P NMR (CD$_3$OD, 300 MHz): δ 42.91. LCMS m/z: [M+H]$^+$=365.2.

Example 30

{(R)-3-[(S)-2-Amino-3-(1H-imidazol-4-yl)-propionylamino]-2-hydroxy-propyl}-cyclohexylmethyl-phosphinic acid

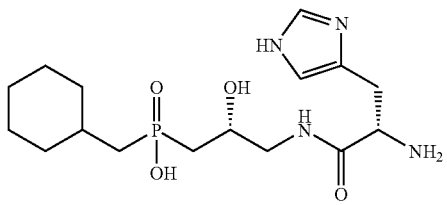

The title compound was prepared substantially following the procedures as set forth in Step 4, Example 1, Method A, and employing ((R)-3-Amino-2-hydroxy-propyl)-cyclohexylmethyl-phosphinic acid benzyl ester hydrochloride and N-Cbz-L-histidine-OH as the starting materials. Subsequent hydrogenation of the resulting product in accordance with the procedures of Step 5, Example 1, Method B, and RP-HPLC purification yielded the title compound. $^1$H NMR (CD$_3$OD, 300 MHz): δ 8.16 (s, 1H), 7.19 (s, 1H), 4.15 (t, 1H), 4.12-3.98 (m, 1H), 3.38-3.10 (m, 4H), 1.94 (br.d 2H), 1.85-1.60 (m, 6H), 1.56 (dd, 2H), 1.40-1.16 (m, 3H), 1.15-0.96 (m, 2H). $^{31}$P NMR (CD$_3$OD, 300 MHz): δ 41.59. LCMS m/z: [M+H]$^+$=373.2

Example 31

Cyclohexylmethyl-((R)-2-hydroxy-3-{(S)-3-phenyl-2-[((S)-pyrrolidine-2-carbonyl)-amino]-propionylamino}-propyl)-phosphinic acid hydrochloride

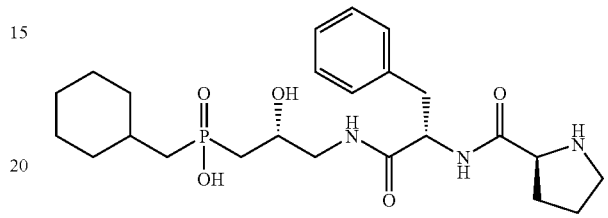

The title compound was prepared substantially following the procedures as set forth in Method B, Example 12, and employing ((R)-3-amino-2-hydroxy-propyl)-cyclohexylmethyl-phosphinic acid benzyl ester hydrochloride and N-Cbz-L-proline-L-phenylalanine-OH as the starting materials. The crude product was purified by RP-HPLC to give the title compound as a white solid. $^1$H NMR (CD$_3$OD, 300 MHz): δ 7.30-7.20 (m, 5H), 4.54 (dd, 1H, J=5.7, 9.3 Hz), 4.15 (t, 1H, J=6.9), 3.98 (m, 1H), 3.38-3.15 (m, 6H), 2.97 (dd, 1H, J=9.6, 13.8 Hz), 2.33 (m, 1H), 1.98 (m, 2H), 1.91 (m, 2H), 1.75-1.60 (m, 6H), 1.52-1.46 (m, 2H), 1.33-1.14 (m, 3H), 1.07-0.90 (m, 2H). $^{31}$P NMR (CD$_3$OD, 300 MHz): δ 42.19. LCMS m/z: [M+H]$^+$=480.3.

Example 32

{(R)-3-[(S)-2-Amino-3-(4-hydroxy-phenyl)-propionylamino]-2-hydroxy-propyl}-cyclohexylmethyl-phosphinic acid

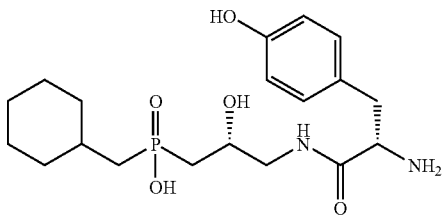

The title compound was prepared substantially following the procedures as set forth in Step 4, Example 1, Method A, and employing ((R)-3-Amino-2-hydroxy-propyl)-cyclohexylmethyl-phosphinic acid benzyl ester hydrochloride and N-Cbz-L-tyrosine-OH as the starting materials. Subsequent hydrogenation of the resulting product in accordance with the procedures of Step 5, Example 1, Method B, and RP-HPLC purification yielded the title compound. $^1$H NMR (CD$_3$OD, 300 MHz): δ 7.11 (d, 2H), 6.78 (d, 2H), 4.14-3.86 (m, 2H), 3.40 (dd, 1H), 3.22-3.03 (m, 2H), 3.01-2.88 (m, 1H), 1.94 (br.d, 2H), 1.86-1.58 (m, 6H), 1.51 (dd, 2H), 1.40-1.13 (m, 3H), 1.11-0.93 (m, 2H). $^{31}$P NMR (CD$_3$OD, 300 MHz): δ 40.19. LCMS m/z: [M+H]$^+$=399.3.

Example 33

[(R)-3-((S)2-Amino-3-carbamoyl-propionylamino)-2-hydroxy-propyl]-cyclohexylmethyl-phosphinic acid

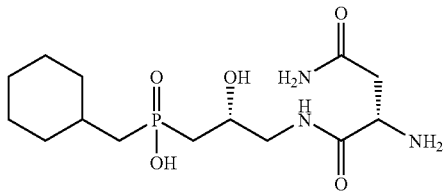

The title compound was prepared substantially following the procedures as set forth in Step 4, Example 1, Method A, and employing ((R)-3-Amino-2-hydroxy-propyl)-cyclohexylmethyl-phosphinic acid benzyl ester hydrochloride and N-Cbz-L-asparagine-OH as the starting materials. Subsequent hydrogenation of the resulting product in accordance with the procedures of Step 5, Example 1, Method B, and RP-HPLC purification yielded the title compound. $^1$H NMR (CD$_3$OD, 300 MHz): δ 4.26-4.13 (m, 1H), 4.12-3.98 (m, 1H), 3.42-3.32 (m, 2H), 2.98-2.71 (m, 2H), 1.93 (br.d, 2H), 1.84-1.58 (m, 6H), 1.51 (dd, 2H), 1.42-1.15 (m, 3H), 1.13-0.94 (m, 2H). $^{31}$P NMR (CD$_3$OD, 300 MHz): δ 40.16. LCMS m/z: [M+H]$^+$=350.3.

Example 34

((R)-3-{(S)-2-[(S)-2-Amino-3-(1H-imidazol-4-yl)-propionylamino]-3-methyl-butyrylamino}-2-hydroxy-propyl)-cyclohexylmethyl-phosphinic acid

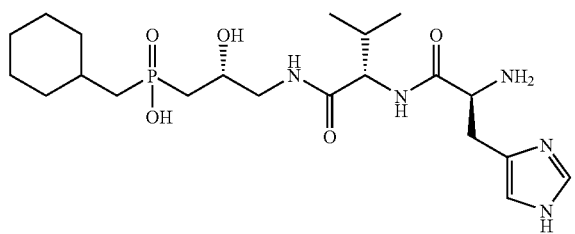

The title compound was prepared substantially following the procedures as set forth in Method B, Example 12, and employing ((R)-3-amino-2-hydroxy-propyl)-cyclohexylmethyl-phosphinic acid benzyl ester hydrochloride and N-Cbz-His-Val-OH as the starting materials, which yielded the title compound as a white powder. $^1$H NMR (CD$_3$OD, 300 MHz): δ 8.47 (s, 1H), 7.25 (s, 1H), 4.25 (t, 1H), 4.10 (d, 1H), 4.0 (m, 1H), 3.6-3.5 (dd, 1H), 3.10-3.00 (m, 2H), 2.09-2.02 (m, 1H), 1.95-1.86 (m, 2H), 1.80-1.54 (m, 8H), 1.41-1.02 (m, 3H), 1.0-0.95 (m, 9H). $^{31}$P NMR (CD$_3$OD, 300 MHz): δ 42.66. LCMS m/z: [M+H]$^+$=472.

Example 35A and 35B

Example 35A

{(R)-3-[(R)-2-((R)-2-Amino-3-methyl-butyrylamino)-3-methyl-butyrylamino]-2-hydroxy-propyl}-cyclohexylmethyl-phosphinic acid, and

Example 35B

{(R)-3-[(S)-2-((R)-2-Amino-3-methyl-butyrylamino)-3-methyl-butyrylamino]-2-hydroxy-propyl}-cyclohexylmethyl-phosphinic acid Example 35A

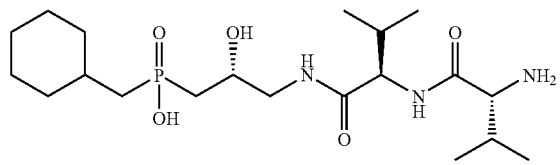

Example 35B

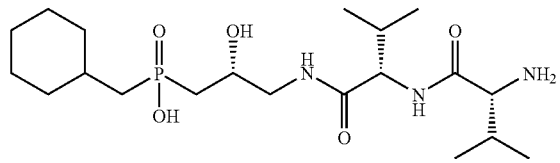

The title compounds were prepared as a mixture of diastereomers from ((R)-3-amino-2-hydroxy-propyl)-cyclohexylmethyl-phosphinic acid benzyl ester hydrochloride, substantially following the procedures as set forth in Method A, Example 12, and using N-Cbz-D-valine-L-valine-OH. The mixture was purified by RP-HPLC using 10-40% CH$_3$CN/(HCl/H$_2$O, pH=3.5) over 18 min at 70 mL/min. The first fraction was lyophilized to give {(R)-3-[(R)-2-((R)-2-amino-3-methyl-butyrylamino)-3-methyl-butyrylamino]-2-hydroxy-propyl}-cyclohexylmethyl-phosphinic acid. $^1$H NMR (CD$_3$OD, 300 MHz): δ 4.21 (d, 1H), 4.15-3.98 (m, 1H), 3.79 (d, 1H), 3.33 (dd, 1H), 3.35-3.18 (m, 1H), 2.30-2.17 (m, 1H), 2.16-2.02 (m, 1H), 1.95 (br.d, 2H), 1.86-1.60 (m, 6H), 1.53 (dd, 2H), 1.40-1.18 (m, 3H), 1.15-0.95 (m, 14H). $^{31}$P NMR (CD$_3$OD, 300 MHz): δ 42.88. LCMS m/z: [M+H]$^+$=434.3. The second fraction gave {(R)-3-[(S)-2-((R)-2-amino-3-methyl-butyrylamino)-3-methyl-butyrylamino]-2-hydroxy-propyl}-cyclohexylmethyl-phosphinic acid. $^1$H NMR (CD$_3$OD, 300 MHz): δ 4.15 (d, 1H), 4.08-3.91 (m, 1H), 3.77 (d, 1H), 3.60-3.45 (m, 1H), 3.23-3.12 (m, 1H), 2.38-2.12 (m, 2H), 1.93 (br.d, 2H), 1.86-1.60 (m, 6H), 1.58-1.45 (m, 2H), 1.43-1.18 (m, 3H), 1.15-0.92 (m, 14H). $^{31}$P NMR (CD$_3$OD, 300 MHz): δ 41.94. LCMS m/z: [M+H]$^+$=434.3.

Example 36A and 36B

Example 36A

{(R)-3-[(R)-2-((R)-2-Amino-3-methyl-butyrylamino)-propionylamino]-2-hydroxy-propyl}-cyclohexylmethyl-phosphinic acid, and

Example 36B

{(R)-3-[(S)-2-((R)-2-Amino-3-methyl-butyrylamino)-propionylamino]-2-hydroxy-propyl}-cyclohexylmethyl-phosphinic acid Example 36A

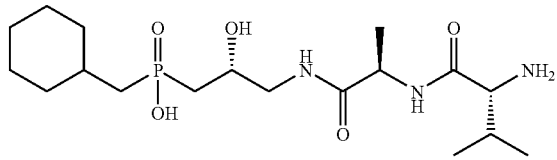

Example 36B

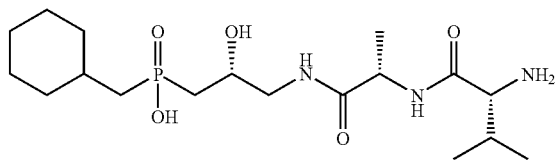

The title compounds were prepared as a mixture of diastereomers from ((R)-3-amino-2-hydroxy-propyl)-cyclohexylmethyl-phosphinic acid benzyl ester hydrochloride, substantially following the procedures as set forth in Method A, Example 12, and using N-Cbz-D-valine-L-alanine-OH. The mixture was purified by RP-HPLC using 10-40% CH$_3$CN/(HCl/H$_2$O, pH=3.5) over 18 min at 70 mL/min. The first fraction was lyophilized to give {(R)-3-[(R)-2-((R)-2-amino-3-methyl-butyrylamino)-propionylamino]-2-hydroxy-propyl}-cyclohexylmethyl-phosphinic acid. $^1$H NMR (CD$_3$OD, 300 MHz): δ 4.38 (q, 1H), 4.12-3.96 (m, 1H), 3.72 (d, 1H), 3.38-3.25 (m, 2H), 2.30-2.17 (m, 1H), 1.93 (br.d, 2H), 1.83-1.60 (m, 6H), 1.53 (dd, 2H), 1.41 (d, 3H), 1.39-1.15 (m, 3H), 1.13-0.97 (m, 8H). $^{31}$P NMR (CD$_3$OD, 300 MHz): δ 42.86. LCMS m/z: [M+H]$^+$=406.3. The second fraction gave {(R)-3-[(S)-2-((R)-2-amino-3-methyl-butyrylamino)-propionylamino]-2-hydroxy-propyl}-cyclohexylmethyl-phosphinic acid. $^1$H NMR (CD$_3$OD, 300 MHz): δ 4.35 (q, 1H), 4.08-3.93 (m, 1H), 3.65 (d, 1H), 3.52 (dd, 1H), 3.23-3.10 (m, 1H), 2.23-2.05 (m, 1H), 1.93 (br.d, 2H), 1.83-1.60 (m, 6H), 1.53 (dd, 2H), 1.42 (d, 3H), 1.40-1.18 (m, 3H), 1.16-0.95 (m, 8H). $^{31}$P NMR (CD$_3$OD, 300 MHz): δ 42.130. LCMS m/z: [M+H]$^+$=406.3.

Example 37

((R)-3-{(S)-2-[(S)-2-((S)-2-Amino-3-methyl-butyrylamino)-3-methyl-butyryl-amino]-3-methyl-butyrylamino}-2-hydroxy-propyl)-cyclohexylmethyl-phosphinic acid

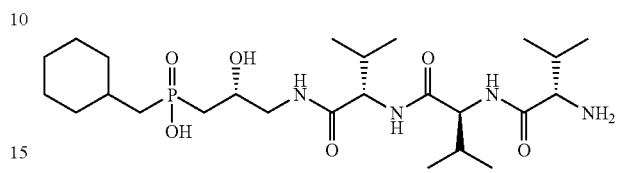

Step 1: {(R)-3-[(S)-2-((S)-2-tert-Butoxycarbonylamino-3-methyl-butyrylamino)-3-methyl-butyrylamino]-2-hydroxy-propyl}-cyclohexylmethyl-phosphinic acid benzyl ester: The title compound was prepared substantially in a similar manner as Example 12 Method B using N-Boc-L-valine-L-valine and ((R)-3-amino-2-hydroxy-propyl)-cyclohexylmethyl phosphinic acid benzyl ester hydrochloride. The crude product was purified by gradient flash chromatography (methanol/methylene chloride) on a RediSep disposable column. $^1$H NMR (CD$_3$Cl, 300 MHz): δ 7.45-7.30 (m, 5H), 6.50 (d, 1H), 5.15-4.98 (m, 3H), 4.55 (br.s, 1H), 4.33-4.22 (m, 1H), 4.20-4.05 (m, 1H), 3.95-3.84 (m, 1H), 3.56-3.40 (m, 1H), 3.38-3.26 (m, 1H), 2.35-2.12 (m, 2H), 1.98-1.79 (m, 4H), 1.78-1.63 (m, 4H), 1.49 (s, 9H), 1.38-1.15 (m, 3H), 1.13-0.85 (m, 14H). $^{31}$P NMR (CD$_3$OD, 300 MHz): δ 59.46, 58.33. LCMS m/z: [M+H]$^+$=624.85.

Step 2: ((R)-3-{(S)-2-[(S)-2-((S)-2-Benzyloxycarbonylamino-3-methyl-butyrylamino)-3-methyl-butyrylamino]-3-methyl-butyrylamino}-2-hydroxy-propyl)-cyclohexylmethyl-phosphinic acid benzyl ester: The resulting product from Step 1 was deprotected in a similar manner as Example 1, step 3, and the compound was used immediately and coupled to N-Cbz-L-valine in accordance with the procedures set forth in Example 12, Method B. The crude product was purified by gradient flash chromatography (methanol/methylene chloride) on a RediSep disposable column. $^1$H NMR (CD$_3$Cl, 300 MHz): δ 7.45-7.25 (m, 10H), 6.0-5.85 (m, 1H), 5.18-4.92 (m, 4H), 4.50-4.33 (m, 2H), 4.31-4.04 (m, 2H), 3.43-3.26 (m, 2H), 2.25-2.03 (m, 3H), 2.02-1.70 (m, 8H), 1.37-1.10 (m, 4H), 1.04-0.82 (m, 20H). LCMS m/z: [M+H]$^+$=757.9.

Step 3: ((R)-3-{(S)-2-[(S)-2-((S)-2-Amino-3-methyl-butyrylamino)-3-methyl-butyrylamino]-3-methyl-butyrylamino}-2-hydroxy-propyl)-cyclohexylmethyl-phosphinic acid: Hydrogenation of ((R)-3-{(S)-2-[(S)-2-((S)-2-Benzyloxycarbonylamino-3-methyl-butyrylamino)-3-methyl-butyrylamino]-3-methyl-butyrylamino}-2-hydroxy-propyl)-cyclohexylmethyl-phosphinic acid benzyl ester according to Example 1, Step 5, Method A gave ((R)-3-{(S)-2-[(S)-2-((S)-2-amino-3-methyl-butyrylamino)-3-methyl-butyrylamino]-3-methyl-butyrylamino}-2-hydroxy-propyl)-cyclohexylmethyl-phosphinic acid. $^1$H NMR (CD$_3$OD, 300 MHz): δ 4.45-4.30 (m, 1H); 4.28-4.20 (m, 1H); 4.11-3.98 (m, 1H); 3.80-3.63 (m, 1H); 3.38-3.20 (m, 2H); 2.29-2.16 (m, 1H); 2.15-1.97 (m, 2H); 1.93 (br d, 2H); 1.80-1.58 (m, 6H); 1.48 (dd, 2H); 1.40-1.16 (m, 3H); 1.10-0.85 (m, 20H). $^{31}$P NMR (CD$_3$OD, 300 MHz): δ 40.2. LCMS m/z: [M+H]$^+$=533.12.

Example 38

((R)-3-{(S)-2-[2-(2-Amino-acetylamino)-acety-lamino]-3-methyl-butyrylamino}-2-hydroxy-propyl)-cyclohexylmethyl-phosphinic acid

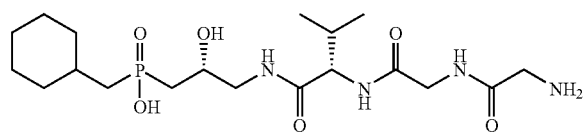

The title compound was prepared substantially following the procedures as set forth in Method B, Example 12, and employing ((R)-3-amino-2-hydroxy-propyl)-cyclohexylmethyl-phosphinic acid benzyl ester hydrochloride and N-Cbz-glycine-glycine-L-valine-OH as the starting materials, which yielded the title compound as a white powder. $^1$H NMR (CD$_3$OD, 300 MHz): δ 4.17 (d, 1H), 4.15-3.82 (m, 3H), 3.75 (s, 2H), 3.40-3.25 (m, 2H), 2.26-2.12 (m, 1H), 1.93 (br.d, 2H), 1.83-1.58 (m, 6H), 1.51 (dd, 2H), 1.41-1.13 (m, 3H), 1.11-0.93 (m, 8H). $^{31}$P NMR (CD$_3$OD, 300 MHz): δ 40.60. LCMS m/z: [M+H]$^+$=449.4.

BIOLOGICAL EXAMPLES

Example 39

This Example 39 demonstrates the improved bioavailability of the compounds of the present invention.
Animals: Male CD1 mice (Charles River) weighing about 25 g—with free access to food and water.
Dose Groups: The compounds of this invention were administered to the test animals at a dose, which is molar equivalent to 10 mg/kg of the parent compound 1, ((R)-3-amino-2-hydroxy-propyl)-cyclohexylmethyl-phosphinic acid. Each of the test compounds was formulated at this dose level to yield a dose volume of 10 mL/kg and administered by oral gavage to a group of three mice per time point in each study group.
Formulations: The compounds of this invention were dissolved in vehicle of 0.2% Tween 80 and 0.5% methylcellulose (MC) at a concentration of about 1 mg/mL.
Samples: The blood samples (for plasma) were collected at the following time points: 5, 15 30 and 45 min predose; and 1, 2, 3, 4, 5, and 7 hrs post-dose. Brains were collected at 2, 4 and 7 hrs post-dose
Blood Handling: The blood samples were added to tubes containing 20 μL of a stock 10 mg/ml solution of sodium fluoride. The blood tubes were then stored in a refrigerator at approximately about 4° C. The volume of blood in each of these samples was about 0.4 mL. The samples were then centrifuged in a refrigerated centrifuge. The plasma samples were then stored in a freezer maintained at about −20° C.
Brain Handling: The brains were removed following dissection of the animals at the specified time intervals and stored on dry ice and transferred to a freezer maintained at about −20° C. Each of the mouse brain was first homogenized with 3.0 mL of 25% acetonitrile before using for bioanalysis as described below.
Bioanalysis: All plasma and brain samples were then analyzed for concentrations of the test compound as well as the parent compound 1, ((R)-3-amino-2-hydroxy-propyl)-cyclohexylmethyl-phosphinic acid by LC/MS/MS. The relative amounts of parent compound 1, ((R)-3-amino-2-hydroxy-propyl)-cyclohexylmethyl-phosphinic acid, observed in the plasma for each of the test compounds of this invention are summarized in Table 2.

TABLE 2

| EXAMPLE NO. | Percent Relative Bioavailability of compound 1 in plasma* |
|---|---|
| 1 | 219 |
| 2 | 155 |
| 3 | 127 |
| 4 | 1.2 |
| 5 | 97 |
| 6 | 122 |
| 7 | 38 |
| 8 | 154 |
| 9 | 99 |
| 10A | 234 |
| 14 | 228 |
| 15A | 197 |
| 17A | 311 |
| 21 | 1.3 |

*Relative to the bioavailability of the parent compound when dosed as itself.

The analyses of the brain samples by LC/MS/MS showed that the concentration of the parent compound 1 in brain was proportional to the concentration of the parent compound in plasma. Whereas, in most cases, the levels of the test compound was too small to be detected for all of the test compounds analyzed.

Example 40

Porsolt's Forced Swim Test

The effects measured in this model have been correlated to antidepressant efficacy for drugs. The paradigm of his model is that an effective antidepressant compound will cause a rat to make greater attempts to escape a water-filled cylinder than a rat given vehicle only.

Animals used in this study are non-naive male Sprague Dawley rats weighing between 225-350 grams. The test apparatus consists of 6 clear PLEXIGLAS® cylinders 40 cm high×19 cm wide. Cylinders are filled to 18 cm with 25° C. water. Each rat is placed in a cylinder for a 15 minute training session. Following either subchronic or acute dosing of either vehicle (0.5% methylcellulose) or compound, animals are brought back 24 hours lather for a 5 minute test session. These test sessions are videotaped for later scoring.

Subchronic dosing consists of administering drug three times in the 24-hour period between training and testing. The drug is administered 24 hrs., 5 hrs., and 1 hr. prior to the test session. Acute dosing consists of administering the drug once, 1 hour prior to the test session. Scoring is done using a time-sampling computer program. Every five seconds, animals are rated as demonstrating one of three behaviors: immobility, mild swim, or climbing. These sampling scores are then converted into percentages of the test session.

Example 41

Social Conflict Test

The effects measured in this model have been correlated either to antidepressant efficacy and/or anxiety efficacy for drugs. This test provides complex measures for prediction of anxiolytic and anxiogenic activity of drugs in behaviorally different groups of animals.

Male albino random-bred mice, weighing 18-20 g are used in this study. They are housed singly in self cleaning cages or in groups of ten. The cages used for the individual housing are made of solid metal walls 13 cm high with wire mesh floors (8×17 cm), which are placed 3 cm above trays with wood shavings. This wire-mesh floor ensured that the isolates are not handled throughout the period of single housing. The mice kept in groups are housed in large standard plastic cages (26×42×15 cm) with floors covered with wood shavings. All mice are housed under room lighting (with lights on from 0600 hours to 1800 hours) and under temperature ranging from 22° C. to 24° C. Food and water are available ad libitum.

The mice are observed in transparent cages (20×30×20 cm) with wood shavings on the floor and tops covered with transparent covers with apertures for air. The observations are performed under moderate room lighting from 0800 hours to 1300 hours.

Social interaction tests are started after 3 weeks of isolation and involve one singly housed mouse paired with the same group housed mouse. The isolates are allowed 15 min adaptation in the observational cages before the group-housed partners are introduced; the interaction ends after 4 min. This procedure, which suppresses aggression in group-housed mice and reduces their social behavior, facilitates active social behavior in isolates. The observation cages are cleaned and their floors are covered with new wood shavings after each interaction.

All subjects undergo four social interaction tests at 1-week intervals. The isolates are given a particular dose of the compounds of this invention (usually at about 1 mg/kg) or vehicle in a randomized order, while the group-housed partners remained untreated. The group-housed mice served only to stimulate social behavior in the isolates. In the event that a group-housed 'stimulus' mouse attacks the isolated mouse, the pair is excluded from the experiment.

The behavior of animals during the interactions are recorded on videotape. The tapes are later analyzed by an observer with no knowledge of the drug treatment. The frequency, total duration and latency of a number of aggressive, defensive-escape (timid), social and locomotor activities are recorded. Changes in social interaction time and total activity are then determined by comparing the means of the test compound administered groups to the vehicle control groups.

The social activities include the social sniff—sniffing the partner's head, body, genitals or tail; climb—the mouse places its forepaws on the partner's back, mostly in the shoulder region, and usually sniffs this area at the same time; and follow—following the partner by quiet walking.

The aggressive activities include attack—a fierce lunging at the partner often associated with biting; threat—a sideways or an upright stance with head and forebody movements toward the partner, and trying to bite the partner (offensive sideways or upright posture); and tail rattle—rapid vibration of the tail.

The timid activities include defense—the mouse responds to the partner's social behavior by raising forepaws, hunching the back (defensive upright posture) or by some rotation of the body bringing the legs closest to the other animal off the ground (defensive sideways posture); escape—a rapid running or jumping away from the partner; and alert posture—a sudden interruption of all movements with eyes and ears being directed toward the partner.

Locomotor activities include walk—any walking across the cage that is not apparently related to the partner; and rear—the mouse stands only on his hind legs and usually sniffs air or walls at the same time.

Example 42

Chronic Mild Stress Model (CMS)

The following CMS study is performed using the parent compound 1 (hereafter "compound 1") in comparison to known anti-depressant compound imipramine.

Male Wistar rats are brought into the laboratory two months before the start of the experiment at which time they weighed approximately 300 grams. Except as described below, the animals are singly housed, with food and water freely available, and maintained on a 12 hour light/dark cycle (lights on at 8 AM) at a temperature of about 22° C.

The animals are first trained to consume a 1% sucrose solution; training consists of eight 1 hour baseline tests in which sucrose is presented, in the home cage, following 14 hours food and water deprivation; intake is measured by weighing pre-weighed bottles containing the sucrose solution at the end of the test. Subsequently, sucrose consumption is monitored, under similar conditions, at weekly intervals throughout the whole experiment.

On the basis of their sucrose intakes in the final baseline test, the animals are divided into two matched groups. One group of animals is subjected to a chronic mild stress procedure for a period of 9 consecutive weeks. Each week of stress regime consisted of: two periods of food or water deprivation (12 and 14 hour), two periods of 45 degree cage tilt (12 and 14 hour+), two periods of intermittent overnight illumination (lights on and off every 2 hours), two 14 hour periods of soiled cage (200 ml water in sawdust bedding), two 14 hour periods of paired housing, two 14 hour periods of low intensity stroboscopic illumination (150 flashes/min). Stressors are applied continuously throughout the day and night, and scheduled randomly. Control animals are housed in a separate room and have no contact with the stressed animals. They are deprived of food and water for the 14 hours preceding each sucrose test, but otherwise food and water are freely available in the home cage. On the basis of their sucrose intake scores following 3 weeks of stress, both stressed and control animals are each divided further into matched subgroups (n=8), and for subsequent five weeks they receive daily administrations of vehicle (1 ml/kg, intraperitoneally (ip)) imipramine (10 mg/kg, ip) or compound 1 (3 and 30 mg/kg orally). All drug injections are in a volume of 1 ml/kg body weight. Drugs are administered at 10 AM and sucrose tests are carried out 24 hours following the last drug treatment. After five weeks, the treatments are terminated and after one week of withdrawal a final sucrose test is carried out. Stress is continued throughout the period of treatment and withdrawal.

Results are analyzed by multiple analysis of variance, followed by Fisher's LSD test for post hoc comparisons of means. The activity of compound 1 at the tested dose level of 3 and 30 mg/kg is equal to that of imipramine.

Example 43

Object Recognition Test

The object recognition test is a memory test. It measures the ability of mice (and rats) to differentiate between known and unknown objects and is therefore suitable for the determination of the memory-improving action of the compounds according to the invention.

The test can generally be carried out as described in the literature. (Blokland et al. NeuroReport 1998, 9, 4205-4208; Ennaceur, A., Delacour, J., Behav. Brain Res. 1988, 31, 47-59; Ennaceur, A., Meliani, K., Psychopharnacology 1992, 109, 321-330; Prickaerts, et al. Eur. J. Pharmacol. 1997, 337, 125-136).

In a first passage, a mouse in an otherwise empty relatively large observation arena is confronted with two identical objects. The mouse will extensively examine, i.e. sniff and touch, both objects. In a second passage, after an interval of 24 hours, the mouse is again tested in the observation arena. One of the known objects is now replaced by a new, unknown object. When a mouse recognizes the known object, it will especially examine the unknown object. After 24 hours, a mouse, however, has normally forgotten which object it has already examined in the first passage, and will therefore inspect both objects equally intensively. The administration of a substance having learning- and memory-improving action will lead to a mouse recognizing the object already seen 24 hours beforehand, in the first passage, as known. It will examine the new, unknown object in greater detail than the already known one. This memory power is expressed in a discrimination index. A discrimination index of zero means that the mouse examines both objects, the old and the new one, for the same length of time; i.e. it has not recognized the old object and reacts to both objects as if they were both unknown and new. A discrimination index of greater than zero means that the mouse has inspected the new object for longer than the old one; i.e. the mouse has recognized the old object.

Under these conditions, Example 1 shows an effect at a dose in the range of 0.03 to 0.1 mg/kg of body weight.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound, including enantiomers, stereoisomers, and tautomers of said compound and pharmaceutically acceptable salts thereof, with said compound having the general structure shown in formula I:

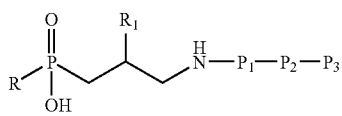
(I)

wherein:
R is $C_{1-8}$alkyl, $C_{3-8}$cycloalkyl$C_{1-4}$alkyl, aryl$C_{1-4}$alkyl or fluoroalkyl of the formula $C_nH_xF_y$, wherein n is an integer from 1 to 4, x is an integer from 0 to 8, y is an integer from 1 to 9 and sum of x and y is 2n+1;
$R_1$ is hydrogen or hydroxy;
$P_1$ and $P_2$ are a bond; and
$P_3$ is Gly, D- or L-Ala, Ile, Leu, Lys, Phe, Pro, Trp, Tyr, Val, Nval, Nle, Sar, Ser, bAla, bVal, Met, Orn, Thr, Cys, His, Arg, Asp, Glu, Asn and Gln.

2. The compound as set forth in claim 1, wherein said compound is of the formula IB:

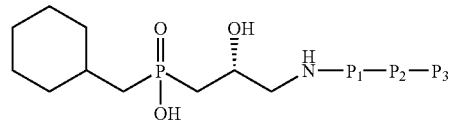
(IB)

wherein $P_1$, $P_2$ and $P_3$ are as defined in claim 1.

3. The compound as set forth in claim 1, wherein:
$P_3$ is Gly, L-Ala, L-Leu, L-Ile, L-Phe, L-Pro, L-Val, L-Thr, L-Glu, L-His, L-Tyr, L-Asp and L-Asn.

4. The compound as set forth in claim 1, wherein:
$P_3$ is Gly, L-Ala, L-Leu, L-Ile, L-Phe, L-Thr, and L-Val.

5. The compound as set forth in claim 1, wherein:
$P_3$ is Gly, L-Ala, L-Ile, L-Thr, and L-Val.

6. The compound as set forth in claim 1, wherein:
$P_3$ is Gly, L-Thr, and L-Val.

7. The compound as set forth in claim 1, which is selected from the group consisting of:
  [(R)-3-((S)-2-amino-3-methyl-butyrylamino)-2-hydroxy-propyl]-cyclohexylmethyl-phosphinic acid;
  [(R)-3-(2-amino-acetylamino)-2-hydroxy-propyl]-cyclohexylmethyl-phosphinic acid;
  [(R)-3-((S)-2-amino-propionylamino)-2-hydroxy-propyl]-cyclohexylmethyl-phosphinic acid;
  [(R)-3-((R)-2-amino-3-methyl-butyrylamino)-2-hydroxy-propyl]-cyclohexylmethyl-phosphinic acid;
  [(R)-3-((S)-2-amino-4-methyl-pentanoylamino)-2-hydroxy-propyl]-cyclohexylmethyl-phosphinic acid;
  [(R)-3-((S)-2-amino-3-methyl-pentanoylamino)-2-hydroxy-propyl]-cyclohexylmethyl-phosphinic acid;
  cyclohexylmethyl-{(R)-2-hydroxy-3-[((S)-pyrrolidine-2-carbonyl)-amino]-propyl}-phosphinic acid;
  [(R)-3-((S)-2-amino-3-hydroxy-butyrylamino)-2-hydroxy-propyl]-cyclohexylmethyl-phosphinic acid;
  [(R)-3-((S)-2-amino-3-phenyl-propionylamino)-2-hydroxy-propyl]-cyclohexylmethyl-phosphinic acid trifluoroacetate;
  [(R)-3-((R)-2-amino-propionylamino)-2-hydroxy-propyl]-cyclohexylmethyl-phosphinic acid;
  (S)-4-amino-4-[(R)-3-(cyclohexylmethyl-hydroxy-phosphinoyl)-2-hydroxy-propylcarbamoyl]-butyric acid;
  {(R)-3-[(S)-2-amino-3-(1H-imidazol-4-yl)-propionylamino]-2-hydroxy-propyl}-cyclohexylmethyl-phosphinic acid;
  {(R)-3-[(S)-2-amino-3-(4-hydroxy-phenyl)-propionylamino]-2-hydroxy-propyl}-cyclohexylmethyl-phosphinic acid;
  [(R)-3-((S)-2-amino-3-carbamoyl-propionylamino)-2-hydroxy-propyl]-cyclohexylmethyl-phosphinic acid; and
  a pharmaceutically acceptable salt, or hydrate thereof.

8. The compound as set forth in claim 1, which is selected from the group consisting of:
  [(R)-3-((S)-2-amino-3-methyl-butyrylamino)-2-hydroxy-propyl]-cyclohexyl methyl-phosphinic acid;
  [(R)-3-(2-amino-acetylamino)-2-hydroxy-propyl]-cyclohexylmethyl-phosphinic acid;
  [(R)-3-((S)-2-amino-propionylamino)-2-hydroxy-propyl]-cyclohexylmethyl-phosphinic acid;
  [(R)-3-((S)-2-amino-4-methyl-pentanoylamino)-2-hydroxy-propyl]-cyclohexylmethyl-phosphinic acid;
  [(R)-3-((S)-2-amino-3-methyl-pentanoylamino)-2-hydroxy-propyl]-cyclohexylmethyl-phosphinic acid;
  [(R)-3-((S)-2-amino-3-hydroxy-butyrylamino)-2-hydroxy-propyl]-cyclohexylmethyl-phosphinic acid;

[(R)-3-((S)-2-amino-3-phenyl-propionylamino)-2-hydroxy-propyl]-cyclohexylmethyl-phosphinic acid trifluoroacetate; and a pharmaceutically acceptable salt, or hydrate thereof.

9. The compound as set forth in claim 1, which is selected from the group consisting of:
[(R)-3-((S)-2-amino-3-methyl-butyrylamino)-2-hydroxy-propyl]-cyclohexylmethyl-phosphinic acid;
[(R)-3-(2-amino-acetylamino)-2-hydroxy-propyl]-cyclohexylmethyl-phosphinic acid;
[(R)-3-((S)-2-amino-propionylamino)-2-hydroxy-propyl]-cyclohexylmethyl-phosphinic acid;
[(R)-3-((S)-2-amino-3-methyl-pentanoylamino)-2-hydroxy-propyl]-cyclohexylmethyl-phosphinic acid;
[(R)-3-((S)-2-amino-3-hydroxy-butyrylamino)-2-hydroxy-propyl]-cyclohexylmethyl-phosphinic acid; and
a pharmaceutically acceptable salt, or hydrate thereof.

10. The compound as set forth in claim 1, which is [(R)-3-((S)-2-amino-3-methyl-butyrylamino)-2-hydroxy-propyl]-cyclohexylmethyl-phosphinic acid or a pharmaceutically acceptable salt, or hydrate thereof.

11. The compound as set forth in claim 1, which is [(R)-3-(2-amino-acetylamino)-2-hydroxy-propyl]-cyclohexylmethyl-phosphinic acid or a pharmaceutically acceptable salt, or hydrate thereof.

12. The compound as set forth in claim 1, which is [(R)-3-((S)-2-amino-3-hydroxy-butyrylamino)-2-hydroxy-propyl]-cyclohexyl methyl-phosphinic acid or a pharmaceutically acceptable salt, or hydrate thereof.

13. A pharmaceutical composition comprising one or more compounds of formula I, including enantiomers, stereoisomers, and tautomers of said compound and pharmaceutically acceptable salts thereof, in combination with one or more pharmaceutically acceptable carriers, diluents or excipients:

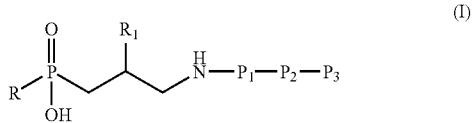
(I)

wherein:
R is $C_{1-8}$alkyl, $C_{3-8}$cycloalkyl$C_{1-4}$alkyl, aryl$C_{1-4}$alkyl or fluoroalkyl of the formula $C_nH_xF_y$, wherein n is an integer from 1 to 4, x is an integer from 0 to 8, y is an integer from 1 to 9 and sum of x and y is 2n+1;
$R_1$ is hydrogen or hydroxy;
$P_1$ and $P_2$ are a bond; and
$P_3$ is Gly, D- or L-Ala, Ile, Leu, Lys, Phe, Pro, Trp, Tyr, Val, Nval, Nle, Sar, Ser, bAla, bVal, Met, Orn, Thr, Cys, His, Arg, Asp, Glu, Asn and Gln.

14. The composition as set forth in claim 13, wherein said compound is selected from the group consisting of:
[(R)-3-((S)-2-amino-3-methyl-butyrylamino)-2-hydroxy-propyl]-cyclohexylmethyl-phosphinic acid;
[(R)-3-(2-amino-acetylamino)-2-hydroxy-propyl]-cyclohexylmethyl-phosphinic acid;
[(R)-3-((S)-2-amino-propionylamino)-2-hydroxy-propyl]-cyclohexylmethyl-phosphinic acid;
[(R)-3-((R)-2-amino-3-methyl-butyrylamino)-2-hydroxy-propyl]-cyclohexylmethyl-phosphinic acid;
[(R)-3-((S)-2-amino-4-methyl-pentanoylamino)-2-hydroxy-propyl]-cyclohexylmethyl-phosphinic acid;
[(R)-3-((S)-2-amino-3-methyl-pentanoylamino)-2-hydroxy-propyl]-cyclohexylmethyl-phosphinic acid;
cyclohexylmethyl-{(R)-2-hydroxy-3[((S)-pyrrolidine-2-carbonyl)-amino]-propyl}-phosphinic acid;
[(R)-3-((S)-2-amino-3-hydroxy-butyrylamino)-2-hydroxy-propyl]-cyclohexylmethyl-phosphinic acid;
[(R)-3-((S)-2-amino-3-phenyl-propionylamino)-2-hydroxy-propyl]-cyclohexylmethyl-phosphinic acid trifluoroacetate;
[(R)-3-((R)-2-amino-propionylamino)-2-hydroxy-propyl]-cyclohexylmethyl-phosphinic acid;
(S)-4-amino-4-[(R)-3-(cyclohexylmethyl-hydroxy-phosphinoyl)-2-hydroxy-propylcarbamoyl]-butyric acid;
{(R)-3-[(S)-2-amino-3-(1H-imidazol-4-yl)-propionylamino]-2-hydroxy-propyl}-cyclohexylmethyl-phosphinic acid;
{(R)-3-[(S)-2-amino-3-(4-hydroxy-phenyl)-propionylamino]-2-hydroxy-propyl}-cyclohexylmethyl-phosphinic acid;
[(R)-3-((S)-2-amino-3-carbamoyl-propionylamino)-2-hydroxy-propyl]-cyclohexylmethyl-phosphinic acid; and
a pharmaceutically acceptable salt, or hydrate thereof.

15. The composition as set forth in claim 13, wherein said compound is selected from the group consisting of:
[(R)-3-((S)-2-amino-3-methyl-butyrylamino)-2-hydroxy-propyl]-cyclohexyl methyl-phosphinic acid;
[(R)-3-(2-amino-acetylamino)-2-hydroxy-propyl]-cyclohexylmethyl-phosphinic acid;
[(R)-3-((S)-2-amino-propionylamino)-2-hydroxy-propyl]-cyclohexylmethyl-phosphinic acid;
[(R)-3-((S)-2-amino-4-methyl-pentanoylamino)-2-hydroxy-propyl]-cyclohexylmethyl-phosphinic acid;
[(R)-3-((S)-2-amino-3-methyl-pentanoylamino)-2-hydroxy-propyl]-cyclohexylmethyl-phosphinic acid;
[(R)-3-((S)-2-amino-3-hydroxy-butyrylamino)-2-hydroxy-propyl]-cyclohexylmethyl-phosphinic acid;
[(R)-3-((S)-2-amino-3-phenyl-propionylamino)-2-hydroxy-propyl]-cyclohexylmethyl-phosphinic acid trifluoroacetate; and
a pharmaceutically acceptable salt, or hydrate thereof.

16. The composition as set forth in claim 13, wherein said compound is selected from the group consisting of:
[(R)-3-((S)-2-amino-3-methyl-butyrylamino)-2-hydroxy-propyl]-cyclohexyl methyl-phosphinic acid;
[(R)-3-(2-amino-acetylamino)-2-hydroxy-propyl]-cyclohexylmethyl-phosphinic acid;
[(R)-3-((S)-2-amino-propionylamino)-2-hydroxy-propyl]-cyclohexylmethyl-phosphinic acid;
[(R)-3-((S)-2-amino-3-methyl-pentanoylamino)-2-hydroxy-propyl]-cyclohexylmethyl-phosphinic acid;
[(R)-3-((S)-2-amino-3-hydroxy-butyrylamino)-2-hydroxy-propyl]-cyclohexylmethyl-phosphinic acid; and
a pharmaceutically acceptable salt, or hydrate thereof.

17. The composition as set forth in claim 13, wherein said compound is [(R)-3-((S)-2-amino-3-methyl-butyrylamino)-2-hydroxy-propyl]-cyclohexylmethyl-phosphinic acid or a pharmaceutically acceptable salt, or hydrate thereof.

18. The composition as set forth in claim 13, wherein said compound is [(R)-3-(2-amino-acetylamino)-2-hydroxy-propyl]-cyclohexylmethyl-phosphinic acid or a pharmaceutically acceptable salt, or hydrate thereof.

19. The composition as set forth in claim 13, wherein said compound is [(R)-3-((S)-2-amino-3-hydroxy-butyrylamino)-2-hydroxy-propyl]-cyclohexylmethyl-phosphinic acid or a pharmaceutically acceptable salt, or hydrate thereof.

20. A method of treating a disease in a patient comprising administering to said patient a therapeutically effective amount of a compound of formula I, including enantiomers, stereoisomers, and tautomers of said compound and pharmaceutically acceptable salts thereof, optionally in combination with one or more pharmaceutically acceptable carriers, diluents or excipients:

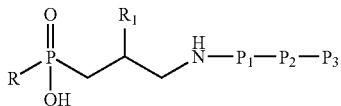

(I)

wherein:
R is $C_{1-8}$alkyl, $C_{3-8}$cycloalkyl$C_{1-4}$alkyl, aryl$C_{1-4}$alkyl or fluoroalkyl of the formula $C_nH_xF_y$, wherein n is an integer from 1 to 4, x is an integer from 0 to 8, y is an integer from 1 to 9 and sum of x and y is 2n+1;
$R_1$ is hydrogen or hydroxy;
$P_1$ and $P_2$ are a bond; and
$P_3$ is Gly, D- or L-Ala, Ile, Leu, Lys, Phe, Pro, Trp, Tyr, Val, Nval, Nle, Sar, Ser, bAla, bVal, Met, Orn, Thr, Cys, His, Arg, Asp, Glu, Asn and Gln; and
wherein said disease is selected from the group consisting of: depression, bipolar disorders, anxiety disorders, psychiatric symptoms, cognitive impairment, and schizophrenia.

21. The method as set forth in claim 20, wherein said disease is depression.

22. The method as set forth in claim 20, wherein said depression is selected from the group consisting of: major depressive episode, dysthymia, melancholia, seasonal affective disorders and depression arising from pre-menstrual tension and adolescence.

23. The method as set forth in claim 20, wherein said disease is anxiety disorders.

24. The method as set forth in claim 23, wherein said anxiety disorders is selected from the group consisting of: panic attack, social phobia, obsessive compulsive disorder, posttraumatic stress disorder and generalized anxiety disorder.

25. The method as set forth in claim 23, wherein said disease is psychiatric symptoms.

26. The method as set forth in claim 25, wherein said psychiatric symptoms are selected from the group consisting of: anger, rejection sensitivity and lack of mental or physical energy.

27. The method as set forth in claim 25, wherein said psychiatric symptoms are associated with premenstrual disorders.

28. The method as set forth in claim 27, wherein said psychiatric symptoms associated with menstrual disorders are selected from the group consisting of: anger, rejection sensitivity and lack of mental or physical energy.

29. The method as set forth in claim 20, wherein said compound is selected from the group consisting of:
[(R)-3-((S)-2-amino-3-methyl-butyrylamino)-2-hydroxy-propyl]-cyclohexylmethyl-phosphinic acid;
[(R)-3-(2-amino-acetylamino)-2-hydroxy-propyl]-cyclohexylmethyl-phosphinic acid;
[(R)-3-((S)-2-amino-propionylamino)-2-hydroxy-propyl]-cyclohexylmethyl-phosphinic acid;
[(R)-3-((R)-2-amino-3-methyl-butyrylamino)-2-hydroxy-propyl]-cyclohexylmethyl-phosphinic acid;
[(R)-3-((S)-2-amino-4-methyl-pentanoylamino)-2-hydroxy-propyl]-cyclohexylmethyl-phosphinic acid;
[(R)-3-((S)-2-amino-3-methyl-pentanoylamino)-2-hydroxy-propyl]-cyclohexylmethyl-phosphinic acid;
cyclohexylmethyl-{(R)-2-hydroxy-3[((S)-pyrrolidine-2-carbonyl)-amino]-propyl}-phosphinic acid;
[(R)-3-((S)-2-amino-3-hydroxy-butyrylamino)-2-hydroxy-propyl]-cyclohexylmethyl-phosphinic acid;
[(R)-3-((S)-2-amino-3-phenyl-propionylamino)-2-hydroxy-propyl]-cyclohexylmethyl-phosphinic acid trifluoroacetate;
[(R)-3-((R)-2-amino-propionylamino)-2-hydroxy-propyl]-cyclohexylmethyl-phosphinic acid;
(S)-4-amino-4-[(R)-3-(cyclohexylmethyl-hydroxy-phosphinoyl)-2-hydroxy-propylcarbamoyl]-butyric acid;
{(R)-3-[(S)-2-amino-3-(1H-imidazol-4-yl)-propionylamino]-2-hydroxy-propyl}-cyclohexylmethyl-phosphinic acid;
{(R)-3-[(S)-2-amino-3-(4-hydroxy-phenyl)-propionylamino]-2-hydroxy-propyl}-cyclohexylmethyl-phosphinic acid;
[(R)-3-((S)-2-amino-3-carbamoyl-propionylamino)-2-hydroxy-propyl]-cyclohexylmethyl-phosphinic acid; and
a pharmaceutically acceptable salt, or hydrate thereof.

30. The method as set forth in claim 20, wherein said compound is selected from the group consisting of:
[(R)-3-((S)-2-amino-3-methyl-butyrylamino)-2-hydroxy-propyl]-cyclohexyl methyl-phosphinic acid;
[(R)-3-(2-amino-acetylamino)-2-hydroxy-propyl]-cyclohexylmethyl-phosphinic acid;
[(R)-3-((S)-2-amino-propionylamino)-2-hydroxy-propyl]-cyclohexylmethyl-phosphinic acid;
[(R)-3-((S)-2-amino-4-methyl-pentanoylamino)-2-hydroxy-propyl]-cyclohexylmethyl-phosphinic acid;
[(R)-3-((S)-2-amino-3-methyl-pentanoylamino)-2-hydroxy-propyl]-cyclohexylmethyl-phosphinic acid;
[(R)-3-((S)-2-amino-3-hydroxy-butyrylamino)-2-hydroxy-propyl]-cyclohexylmethyl-phosphinic acid;
[(R)-3-((S)-2-amino-3-phenyl-propionylamino)-2-hydroxy-propyl]-cyclohexylmethyl-phosphinic acid trifluoroacetate; and
a pharmaceutically acceptable salt, or hydrate thereof.

31. The method as set forth in claim 20, wherein said compound is selected from the group consisting of:
[(R)-3-((S)-2-amino-3-methyl-butyrylamino)-2-hydroxy-propyl]-cyclohexyl methyl-phosphinic acid;
[(R)-3-(2-amino-acetylamino)-2-hydroxy-propyl]-cyclohexylmethyl-phosphinic acid;
[(R)-3-((S)-2-amino-propionylamino)-2-hydroxy-propyl]-cyclohexylmethyl-phosphinic acid;
[(R)-3-((S)-2-amino-3-methyl-pentanoylamino)-2-hydroxy-propyl]-cyclohexylmethyl-phosphinic acid;
[(R)-3-((S)-2-amino-3-hydroxy-butyrylamino)-2-hydroxy-propyl]-cyclohexylmethyl-phosphinic acid; and
a pharmaceutically acceptable salt, or hydrate thereof.

32. The method as set forth in claim 20, wherein said compound is [(R)-3-((S)-2-amino-3-methyl-butyrylamino)-2-hydroxy-propyl]-cyclohexylmethyl-phosphinic acid or a pharmaceutically acceptable salt, or hydrate thereof.

33. The method as set forth in claim 20, wherein said compound is [(R)-3-(2-amino-acetylamino)-2-hydroxy-propyl]-cyclohexylmethyl-phosphinic acid or a pharmaceutically acceptable salt, or hydrate thereof.

34. The method as set forth in claim 20, wherein said compound is [(R)-3-((S)-2-amino-3-hydroxy-butyrylamino)-2-hydroxy-propyl]cyclohexylmethyl-phosphinic acid or a pharmaceutically acceptable salt, or hydrate thereof.

* * * * *

UNITED STATES PATENT AND TRADEMARK OFFICE
CERTIFICATE OF CORRECTION

| | | |
|---|---|---|
| PATENT NO. | : 8,183,231 B2 | Page 1 of 1 |
| APPLICATION NO. | : 11/552346 | |
| DATED | : May 22, 2012 | |
| INVENTOR(S) | : Yong Mi Choi-Sledeski et al. | |

It is certified that error appears in the above-identified patent and that said Letters Patent is hereby corrected as shown below:

In column 7, line 51, delete "L-Ele," and insert -- L-Ile, --, therefor.

In column 11, line 25, delete "metthyl-" and insert -- methyl- --, therefor.

In column 13, line 52, after "1" insert -- . --.

In column 50, line 36, delete "his" and insert -- this --, therefor.

In column 50, line 47, delete "lather" and insert -- later --, therefor.

In column 53, line 4, delete "Psychopharnacology" and insert -- Psychopharmacology --, therefor.

In column 54, line 57, in claim 8, delete "cyclohexyl methyl" and insert -- cyclohexylmethyl --, therefor.

In column 56, line 24, in claim 15, delete "cyclohexyl methyl" and insert -- cyclohexylmethyl --, therefor.

In column 56, line 42, in claim 16, delete "cyclohexyl methyl" and insert -- cyclohexylmethyl --, therefor.

In column 58, line 24, in claim 30, delete "cyclohexyl methyl" and insert -- cyclohexylmethyl --, therefor.

In column 58, line 42, in claim 31, delete "cyclohexyl methyl" and insert -- cyclohexylmethyl --, therefor.

In column 58, line 62, in claim 34, delete "-propyl]" and insert -- -propyl]- --, therefor.

Signed and Sealed this
Thirtieth Day of October, 2012

David J. Kappos
*Director of the United States Patent and Trademark Office*